United States Patent
Eid et al.

(10) Patent No.: US 11,771,538 B2
(45) Date of Patent: Oct. 3, 2023

(54) INJECTION SYSTEMS AND METHODS

(71) Applicant: Nova-Tech Engineering, LLC, Willmar, MN (US)

(72) Inventors: Elliot D. Eid, Richmond, MN (US); Jeremy J. Imdieke, Willmar, MN (US); Christopher J. Stark, Willmar, MN (US); Matthew R. Biel, Willmar, MN (US); Roger A. Harkess, Willmar, MN (US)

(73) Assignee: Nova-Tech Engineering, LLC, Willmar, MN (US)

( * ) Notice: Subject to any disclaimer, the term of this patent is extended or adjusted under 35 U.S.C. 154(b) by 1002 days.

(21) Appl. No.: 16/610,729

(22) PCT Filed: May 3, 2018

(86) PCT No.: PCT/US2018/030782
§ 371 (c)(1),
(2) Date: Nov. 4, 2019

(87) PCT Pub. No.: WO2018/204572
PCT Pub. Date: Nov. 8, 2018

(65) Prior Publication Data
US 2020/0155289 A1    May 21, 2020

Related U.S. Application Data

(60) Provisional application No. 62/502,099, filed on May 5, 2017.

(51) Int. Cl.
*A61D 1/02*   (2006.01)
*A61D 7/00*   (2006.01)
(Continued)

(52) U.S. Cl.
CPC ............... *A61D 1/025* (2013.01); *A61D 7/00* (2013.01); *A61M 5/001* (2013.01); *A61M 5/20* (2013.01);
(Continued)

(58) Field of Classification Search
CPC ..................................... A61D 1/025
See application file for complete search history.

(56) References Cited

U.S. PATENT DOCUMENTS 4,681,565 A   7/1987   Gourlandt
4,758,227 A   7/1988   Lancaster, Jr. et al.
(Continued)

FOREIGN PATENT DOCUMENTS

CN   2250126   3/1997
CN   1406639   4/2003
(Continued)

OTHER PUBLICATIONS

Office Action issued in India for Application No. 201917044799 dated Feb. 23, 2022 (8 pages).
(Continued)

*Primary Examiner* — Jessica B Wong
(74) *Attorney, Agent, or Firm* — Mueting Raasch Group

(57) ABSTRACT

Injection systems and methods of using the same are described herein. Each injection system may include one, two, or more needles, with each needle being configured to move needle between an injection position and a retracted position to deliver an inoculant. The injection needles may rotate about a carriage axis that extends through the injection axis along which each needle moves when moving between their injection and retracted positions. The injection needles in systems that include two or more injection needles may be advanced from the retracted position to the injection position at the same or different times.

32 Claims, 16 Drawing Sheets

(51) Int. Cl.
*A61M 5/00* (2006.01)
*A61M 5/20* (2006.01)
*A61M 5/32* (2006.01)
*A61M 5/46* (2006.01)

(52) U.S. Cl.
CPC ............... *A61M 5/326* (2013.01); *A61M 5/46* (2013.01); *A61M 2005/206* (2013.01); *A61M 2250/00* (2013.01)

(56) References Cited

U.S. PATENT DOCUMENTS

| | | | |
|---|---|---|---|
| 5,651,731 | A | 7/1997 | Gorans et al. |
| 7,232,450 | B2 | 6/2007 | Gorans et al. |
| 7,363,881 | B2 | 4/2008 | Gorans et al. |
| 7,367,284 | B2 | 5/2008 | Gorans |
| 8,211,058 | B2 | 7/2012 | Joma |
| 8,293,298 | B2 * | 10/2012 | Van Esbroeck .... A22C 21/0061 426/442 |
| 9,510,783 | B2 | 12/2016 | Oannou |
| 10,278,797 | B2 | 5/2019 | Gorans |
| 10,350,041 | B2 | 7/2019 | Samson |
| 10,688,256 | B2 | 6/2020 | Limaye |
| 2009/0157038 | A1 | 6/2009 | Jones |
| 2012/0012070 | A1 | 1/2012 | Gorans et al. |
| 2014/0031790 | A1 | 1/2014 | Johnson |
| 2015/0327520 | A1 * | 11/2015 | Van De Zande .... A01K 45/007 119/6.8 |
| 2016/0051352 | A1 | 2/2016 | Moons |
| 2019/0133734 | A1 | 5/2019 | Erickson et al. |
| 2020/0155289 | A1 | 5/2020 | Eid |

FOREIGN PATENT DOCUMENTS

| | | |
|---|---|---|
| CN | 101848684 | 9/2010 |
| CN | 102292048 | 11/2011 |
| CN | 103222901 | 7/2013 |
| CN | 103402459 A | 11/2013 |
| CN | 105705115 | 11/2013 |
| CN | 204428546 | 7/2015 |
| CN | 205073437 | 3/2016 |
| CN | 205144788 | 4/2016 |
| CN | 209595956 U | 11/2019 |
| WO | WO 2015/077532 | 5/2015 |
| WO | WO 2016/125016 | 8/2016 |

OTHER PUBLICATIONS

Office Action issued in China for Application No. 201810414907.0 dated Jun. 15, 2021 (10 pages).

International Patent Application No. PCT/US2018/030782, filed May 3, 2018 International Preliminary Report on Patentability dated Mar. 20, 2019; 16 pages.

International Patent Application No. PCT/US2018/030782, filed May 3, 2018 International Search Report and Written Opinion, dated Oct. 17, 2018; 21 pages.

International Patent Application No. PCT/US2018/030782, filed May 3, 2018 Invitation to Pay Additional Fees and Partial Search Report, dated Jul. 19, 2018; 15 pages.

* cited by examiner

INJECTION SYSTEMS AND METHODS

RELATED APPLICATION

This application is the § 371 U.S. National Stage of International Application No. PCT/US2018/030782, filed 3 May 2018, which claims the benefit under 35 U.S.C. § 119 of U.S. Provisional Application Ser. No. 62/502,099, filed 5 May 2017, and titled INJECTION SYSTEMS AND METHODS OF USE, the disclosures of which are incorporated herein by reference in their entireties.

Injection systems and methods of using the same are described herein.

The processing of poultry may include activities such as sexing to determine gender, inoculating or otherwise medicating the birds, feeding the birds, weighing the birds, treating the beaks and/or claws of the birds (to, e.g., retard their growth), etc. In some conventional systems, birds are handled manually, i.e., individuals must physically hold the bird to perform the injection process.

When injecting poultry to deliver an inoculant such as, e.g., one or more medications or other therapeutic substance, vitamins, or any other substance that should or could be advantageously delivered subcutaneously, the injection process may be complicated by the smaller size of the birds and their movement. Further, in some instances, it may be desirable to deliver the same or different inoculants to two or more different locations on, e.g., a bird.

SUMMARY

Injection systems and methods of using the same are described herein. Each injection system may include one, two, or more needles, with each needle being configured to move needle between an injection position and a retracted position to deliver an inoculant. The injection needles may rotate about a carriage axis that extends through the injection axis along which each needle moves when moving between their injection and retracted positions. The injection needles in systems that include two or more injection needles may be advanced from the retracted position to the injection position at the same or different times.

Two or more injections at same location on a bird (or other animal) may not be desirable for a variety of reasons. For example, in one or more embodiments, in which the materials being injected are the same, too much injectate at a single location may result in an excessive concentration of the injectate in tissue surrounding the injection site. In one or more alternative embodiments in which two different materials are being injected, mixing of the different materials at the same injection site may be contraindicated and may, for example, cause undesirable biological effects, reduce the efficacy of one or both of the materials being injected, etc. The materials, i.e., injectate, injected using one or more embodiments of the injection systems as described herein may include, e.g., vaccines, medications or other therapeutic substances, vitamins, etc.

One potential advantage of one or more embodiments of the injection systems and methods described herein that include two or more injection needles and associated components is that, in one or more embodiments, the injection units may result in the delivery of injected material to two different locations on a bird or other animal. Such separation of injected material may be advantageous for a variety of reasons as discussed in the preceding paragraph.

Another potential advantage of one or more embodiments of the injection systems and methods described herein is the delivery of atomized sterilizing fluid to the distal ends of the injection needles from a remote atomization chamber. Delivery of atomized sterilizing fluid from a remote atomization chamber reduces the number of fluid components such as valves, etc. that must be located close to the distal ends of the injection needles, thereby, improving consistency in the delivery of the atomized sterilizing fluid. Improved consistency in delivery of the atomized sterilizing fluid may, in one or more embodiments, provide for improvements in sterilization efficacy.

Another potential advantage of the injection systems and methods described herein is that unwanted movement of the injection needles during the injection process may be limited by locating the axis of rotation of a needle carriage on which the injection needles are mounted (for rotation between a standby position and an actuation position in which the injection actually occurs) and the injection axis (along which an injection needle travels between a retracted position and an injection position to perform an injection process) relative to each other as described herein to reduce movement of the injection needles other than along their injection axes. Reductions in such unwanted movement of injection needles during injection processes may reduce bleeding and/or tissue damage at the injection sites.

Still another potential advantage of one or more embodiments of the injection systems and methods described herein may be found in the support offered to the injection needles as they move along their respective injection axes. In particular, support of the injection needles may improve tracking of the distal ends of the injection needles along the injection axes such that deviation of the distal ends of the injection needles from the injection axes is reduced. As noted above, reductions in such unwanted movement of injection needles during injection processes may reduce bleeding and/or tissue damage at the injection sites.

Although the injection systems and methods described herein may be used with birds of any age, they may be particularly useful when used with hatchlings, where "hatchlings" are defined as young birds (e.g., chickens, turkeys, ducks, geese, etc.) with an age of one week or less.

In one aspect, one or more embodiments of an injection system as described herein may include: an injection unit comprising: a first needle assembly comprising a first injection needle and a first needle actuator operably connected to the first injection needle, wherein the first needle actuator is configured to move the first injection needle between an injection position and a retracted position along a first injection axis; a second needle assembly comprising a second injection needle and a second needle actuator operably connected to the second injection needle, wherein the second needle actuator is configured to move the second injection needle between an injection position and a retracted position along a second injection axis; wherein, for injection systems including first and second needle assemblies, a distal end of the first injection needle is spaced apart from a distal end of the second injection needle when the first and second injection needles are in their injection positions by a distance of 1 mm or more, optionally 2 mm or more, or optionally 3 mm or more and, at an optional upper end, 6 mm or less, optionally 4 mm or less, or optionally 2 mm or less; and a bird restraint apparatus operably connected to the injection unit, wherein the bird restraint apparatus is configured to restrain a bird in a selected position relative to the injection unit.

In another aspect, one or more embodiments of an injection system as described herein may include: an injection unit comprising: a first needle assembly comprising a first injection needle and a first needle actuator operably connected to the first injection needle, wherein the first needle actuator is configured to move the first injection needle between an injection position and a retracted position along a first injection axis; a needle carriage operably connected to a carriage actuator, wherein the first needle assembly is mounted on the needle carriage, wherein the carriage actuator is configured to rotate the needle carriage about a carriage axis between a standby position and an actuation position, wherein the first injection needle is configured to contact a bird restrained in the bird restraint when the needle carriage moves into the actuation position, and wherein the first injection needle is positioned subcutaneously in a bird restrained in the bird restraint apparatus when the needle carriage is in its actuation position and the first injection needle is in the injection position, and wherein the carriage axis extends through the first injection axis; and a bird restraint apparatus operably connected to the injection unit, wherein the bird restraint apparatus is configured to restrain a bird in a selected position relative to the injection unit.

In another aspect, one or more embodiments of an injection system as described herein may include: an injection unit comprising: a first needle assembly comprising a first injection needle and a first needle actuator operably connected to the first injection needle, wherein the first needle actuator is configured to move the first injection needle between an injection position and a retracted position along a first injection axis; a second needle assembly comprising a second injection needle and a second needle actuator operably connected to the second injection needle, wherein the second needle actuator is configured to move the second injection needle between an injection position and a retracted position along a second injection axis, wherein, for injection systems including first and second needle assemblies, the first injection axis and the second injection axis are not parallel to each other; and a bird restraint apparatus operably connected to the injection unit, wherein the bird restraint apparatus is configured to restrain a bird in a selected position relative to the injection unit.

In another aspect, one or more embodiments of an injection system as described herein may include: an injection unit comprising: a first needle assembly comprising a first injection needle and a first needle actuator operably connected to the first injection needle, wherein the first needle actuator is configured to move the first injection needle between an injection position and a retracted position along a first injection axis; a second needle assembly comprising a second injection needle and a second needle actuator operably connected to the second injection needle, wherein the second needle actuator is configured to move the second injection needle between an injection position and a retracted position along a second injection axis, wherein, for injection systems including first and second needle assemblies, the first injection axis and the second injection axis are not parallel to each other; and a bird restraint apparatus operably connected to the injection unit, wherein the bird restraint apparatus is configured to restrain a bird in a selected position relative to the injection unit. In one or more embodiments, a distal end of the first injection needle is spaced apart from a distal end of the second injection needle when the first and second injection needles are in their injection positions by a distance of 1 mm or more, optionally 2 mm or more, or optionally 3 mm or more and, at an optional upper end, 6 mm or less, optionally 4 mm or less, or optionally 2 mm or less.

In another aspect, one or more embodiments of an injection system as described herein may include: an injection unit comprising: a first needle assembly comprising a first injection needle and a first needle actuator operably connected to the first injection needle, wherein the first needle actuator is configured to move the first injection needle between an injection position and a retracted position along a first injection axis; optionally, a second needle assembly comprising a second injection needle and a second needle actuator operably connected to the second injection needle, wherein the second needle actuator is configured to move the second injection needle between an injection position and a retracted position along a second injection axis; wherein, for injection systems including first and second needle assemblies, a distal end of the first injection needle is spaced apart from a distal end of the second injection needle when the first and second injection needles are in their injection positions by a distance of 1 mm or more, optionally 2 mm or more, or optionally 3 mm or more and, at an optional upper end, 6 mm or less, optionally 4 mm or less, or optionally 2 mm or less; and a bird restraint apparatus operably connected to the injection unit, wherein the bird restraint apparatus is configured to restrain a bird in a selected position relative to the injection unit.

In another aspect, one or more embodiments of an injection system as described herein may include: an injection unit comprising: a first needle assembly comprising a first injection needle and a first needle actuator operably connected to the first injection needle, wherein the first needle actuator is configured to move the first injection needle between an injection position and a retracted position along a first injection axis; optionally, a second needle assembly comprising a second injection needle and a second needle actuator operably connected to the second injection needle, wherein the second needle actuator is configured to move the second injection needle between an injection position and a retracted position along a second injection axis, wherein, for injection systems including first and second needle assemblies, the first injection axis and the second injection axis are not parallel to each other; and a bird restraint apparatus operably connected to the injection unit, wherein the bird restraint apparatus is configured to restrain a bird in a selected position relative to the injection unit.

In one or more embodiments of injection systems as described herein, the first injection axis and the second injection axis intersect.

In one or more embodiments of injection systems as described herein, the first injection axis and the second injection axis form an included angle greater than zero degrees and less than 180 degrees.

In one or more embodiments of injection systems as described herein, the first injection axis and the second injection axis form an included angle of 30 degrees or less, optionally 25° or less, optionally 20° or less, or optionally 15° or less, and, at an optional lower end, the included angle may be 5° or more, optionally 10° or more, or optionally 15° or more.

In one or more embodiments of injection systems as described herein, the first needle assembly and, optionally, the second needle assembly are mounted on a needle carriage, wherein the needle carriage is operably connected to a carriage actuator, wherein the carriage actuator is configured to rotate the needle carriage about a carriage axis between a standby position and an actuation position, wherein the first and second injection needles are configured to contact a bird restrained in the bird restraint when the needle carriage moves into the actuation position, and wherein the first and second injection needles are positioned subcutaneously in a bird restrained in the bird restraint apparatus when the needle carriage is in its actuation position and the first and second injection needles in their injection positions. In one or more embodiments, the carriage axis extends through the first injection axis and the second injection axis.

In one or more embodiments of injection systems as described herein, the injection unit comprises a needle guide, wherein the needle guide comprises: a first guide passage configured to guide the first injection needle when the first injection needle moves between the injection position and the retracted position; and optionally, a second guide passage configured to guide the second injection needle when the second injection needle moves between the injection position and the retracted position. In one or more embodiments, the first guide passage comprises a distal opening, and wherein a distal end of the first injection needle passes through the distal opening when moving between the injection position and the retracted position; and wherein, optionally, the second guide passage comprises a distal opening, and wherein a distal end of the second injection needle passes through the distal opening of the second guide passage when moving between the injection position and the retracted position.

In one or more embodiments of injection systems as described herein, the first guide passage and the second guide passage are separate and distinct passages in the needle guide.

In one or more embodiments of injection systems as described herein, the first needle assembly, the optional second needle assembly, and the needle guide are mounted on a needle carriage, wherein the needle carriage is configured to rotate about a carriage axis between a standby position and an actuation position, wherein the needle guide is configured to contact a bird restrained in the bird restraint when the needle carriage moves into the actuation position, and wherein the first and second injection needles are positioned subcutaneously in a bird restrained in the bird restraint apparatus when the needle carriage is in its actuation position and the first and second injection needles in their injection positions. In one or more embodiments, the carriage axis extends through the first injection axis and the second injection axis.

In one or more embodiments of injection systems as described herein, the first needle actuator comprises a depth adjustment yoke and support, wherein the depth adjustment and yoke and support are configured to change a location of a distal end of the first injection needle along the first injection axis. In one or more embodiments, rotation of one or both of the depth adjustment yoke and the support about the first injection axis changes a location of a distal end of the first injection needle along the first injection axis. In one or more embodiments, the depth adjustment yoke comprises first and second legs acting on the support, wherein the first and second legs are located on opposite sides of the first injection axis. In one or more embodiments, the first and second legs comprise a different length when measured along the first injection axis and wherein the support comprises a stepped ring comprising a plurality of steps located at different positions along the first injection axis. In one or more embodiments, rotation of one or both of the depth adjustment yoke and the stepped ring about the first injection axis changes a location of a distal end of the first injection needle along the first injection axis.

In one or more embodiments of injection systems as described herein, the second needle actuator comprises a depth adjustment yoke and support, wherein the depth adjustment and yoke and support are configured to change a location of a distal end of the second injection needle along the second injection axis. In one or more embodiments, rotation of one or both of the depth adjustment yoke and the support about the second injection axis changes a location of a distal end of the second injection needle along the second injection axis. In one or more embodiments, the depth adjustment yoke comprises first and second legs acting on the support, wherein the first and second legs are located on opposite sides of the second injection axis.

In one or more embodiments of injection systems as described herein, the support comprises a stepped ring comprising a plurality of steps arranged around the second injection axis and located at different positions along a length of the second injection axis, wherein rotation of the stepped ring and/or the depth adjustment yoke changes a distance between the stepped ring and the depth adjustment yoke. In one or more embodiments, rotation of one or both of the depth adjustment yoke and the stepped ring about the second injection axis changes a location of a distal end of the second injection needle along the second injection axis.

In one or more embodiments of injection systems as described herein, the needle guide comprises a sterilant passage extending between an inlet port and an outlet port, wherein fluid passing through the sterilant passage from the inlet port to the outlet port is directed at a distal end of the first injection needle.

In one or more embodiments of injection systems as described herein, the sterilant passage comprises a first sterilant passage, the inlet port comprises a first inlet port, and the outlet port comprises a first outlet port; and the needle guide comprises a second sterilant passage extending between a second inlet port and a second outlet port, wherein fluid passing through the second sterilant passage from the second inlet port to the second outlet port is directed at a distal end of the second injection needle.

In one or more embodiments of injection systems as described herein, the system further comprises a sterilant delivery apparatus comprising: a pump configured to deliver sterilizing fluid from a reservoir to an atomizing chamber, wherein the atomizing chamber is configured to atomize the sterilizing fluid; and a fluid path configured to deliver the atomized sterilizing fluid from the atomizing chamber onto a distal end of the first injection needle through a sterilant port. In one or more embodiments, the fluid path comprises a first fluid path and the sterilant port comprises a first sterilant port, and wherein the sterilant delivery system comprises a second fluid path configured to deliver atomized sterilizing fluid from the atomizing chamber onto a distal end of the second injection needle through a second sterilant port. In one or more embodiments, the first fluid path comprises a sterilant passage in the needle guide, wherein the sterilant passage extends between an inlet port and a first outlet port, wherein fluid passing through the sterilant passage to the first outlet port is directed at a distal end of the first injection needle; and the second fluid path comprises a sterilant passage in the needle guide, wherein the sterilant passage extends between the inlet port and a second outlet port, wherein fluid passing through the sterilant passage to the second outlet port is directed at a distal end of the second injection needle.

In one or more embodiments of injection systems as described herein, the system further comprises a controller operably connected to the first needle actuator and the second needle actuator, wherein the controller is configured to: actuate the first needle actuator to move the first injection needle from its retracted position to its injection position; and actuate the second needle actuator to move the second injection needle from its retracted position to its injection position. In one or more embodiments, the controller is configured to actuate the first and second needle actuators at the same time. In one or more embodiments, the controller is configured to actuate the first and second needle actuators at different times. In one or more embodiments of injection systems as described herein including a needle carriage and carriage actuator, the controller is operably connected to the carriage actuator, and wherein the controller is configured to actuate the carriage actuator to move the needle carriage between the standby position and the actuation position.

In one or more embodiments of injection systems as described herein including a controller and a sterilant delivery apparatus, the pump is operably connected to the controller, and wherein the controller is configured to operate the pump to deliver sterilizing fluid to the atomizing chamber.

In another aspect, methods of using one or more embodiments of the injection systems described herein may include positioning a bird in the injection system by: restraining a bird in the bird restraint apparatus of an injection system as described herein; moving the bird restraint apparatus to an injection location proximate the injection unit; rotating the needle carriage about the carriage axis from the standby position to the actuation position; wherein the first injection axis of the first needle assembly intersects the bird in the bird restraint apparatus when the needle carriage is in the actuation position; and wherein the carriage axis extends through the first injection axis when the needle carriage is in the standby position and the actuation position.

In another aspect, methods of using one or more embodiments of the injection systems described herein may include positioning a bird in the injection system by: restraining a bird in the bird restraint apparatus of an injection system as described herein; moving the bird restraint apparatus to an injection location proximate the injection unit; rotating the needle carriage about the carriage axis from the standby position to the actuation position; wherein the first injection axis of the first needle assembly and the second injection axis of the second needle assembly intersect the bird in the bird restraint apparatus when the needle carriage is in the actuation position; and wherein the carriage axis extends through the first injection axis when the needle carriage is in the standby position and the actuation position. In one or more embodiments, the carriage axis extends through the second injection axis when the needle carriage is in the standby position and the actuation position.

In another aspect, methods of injecting a bird using one or more embodiments of the injection systems described herein may include: restraining a bird in the bird restraint apparatus of an injection system as described herein; moving the bird restraint apparatus to an injection location proximate the injection unit; advancing the first injection needle to its injection position after moving the bird restraint apparatus to the injection location; optionally, advancing the second injection needle to its injection position after moving the bird restraint apparatus to the injection location; delivering a first selected material to a first location in the bird through the first injection needle after advancing the first injection needle into the injection position; and, optionally, delivering a second selected material to a second location in the bird through the second injection needle after advancing the second injection needle into the injection position.

In one or more embodiments of the methods described herein, the first location and the second location are different.

In one or more embodiments of the methods described herein, the first selected material and the second selected material are the same.

In one or more embodiments of the methods described herein, the first selected material and the second selected material are different.

In one or more embodiments of the methods described herein, the method further comprises: moving the first injection needle from its injection position towards its retracted position after delivering the first selected material; delivering sterilant onto a distal end of the first injection needle after moving the first injection needle from its injection position towards its retracted position; optionally, moving the second injection needle from its injection position towards its retracted position after delivering the second selected material; and, optionally, delivering sterilant onto a distal end of the second injection needle after moving the second injection needle from its injection position towards its retracted position. In one or more embodiments, the first injection needle is moved from its injection position towards its retracted position and the second injection needle is moved from its injection position towards its retracted position at the same time.

In one or more embodiments of the methods described herein, the sterilant is atomized before delivery onto the first injection needle and the second injection needle.

In one or more embodiments of the methods described herein, the sterilant is delivered onto the first injection needle after the first injection needle is in its retracted position.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

Where used herein, the terms "top" and "bottom" are used for reference relative to each other only and, depending on the orientation of the apparatus when used, may or may not accurately describe the relative positions of the recited features with respect to the ground.

The above summary is not intended to describe each embodiment or every implementation of the injection systems and methods of using the same as described herein. Rather, a more complete understanding of the invention will become apparent and appreciated by reference to the following Description of Illustrative Embodiments and claims in view of the accompanying figures of the drawing.

BRIEF DESCRIPTION OF THE VIEWS OF THE DRAWING

Illustrative embodiments of the invention will be further described with reference to the views of the drawing, wherein.

DESCRIPTION OF ILLUSTRATIVE EMBODIMENTS

Figure 1:
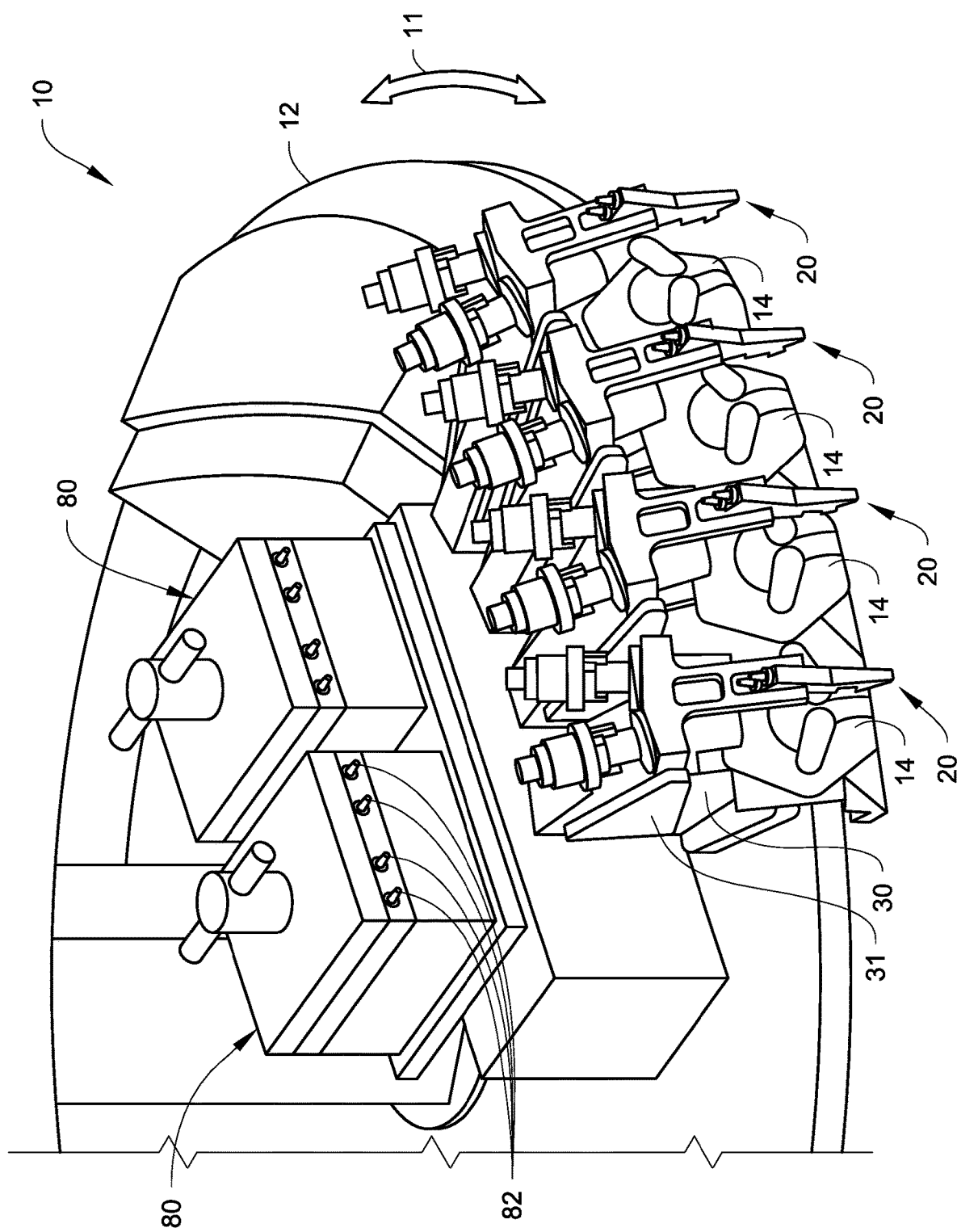
FIG. 1 is a perspective view of a portion of one illustrative embodiment of a poultry processing system that includes a set of four injection systems as described herein.

In the following description of illustrative embodiments, reference is made to the accompanying figures of the drawing which form a part hereof, and in which are shown, by way of illustration, specific illustrative embodiments. It is to be understood that other embodiments may be utilized and structural changes may be made without departing from the scope of the present invention. Further, like reference numbers across the different figures designate the same features in the various figures of the drawing.

One illustrative embodiment of a group of injection systems may be used to deliver injectate materials to birds or other animals is depicted in FIG. 1 where four injection systems are arranged around a bird processing system 10 that includes a stationary base 12 and a rotating turntable (not shown). Although the depicted illustrative embodiment includes a group of four injection systems, bird processing systems including the injection systems described herein may include any selected number of injection systems, e.g., one, two, three, five, etc.

Each of the injection systems includes an injection unit 20 attached to the stationary base 12 of the processing system 10 using a base 30 and arms 31 supporting the injection units 20. The bird restraint apparatus 14 are, in the depicted illustrative embodiment moved into and out of position relative to the injection units 20 in one or both of the directions of bidirectional arrow 11. Also depicted in FIG. 1 are a pair of sterilant delivery apparatus 80 including outlets 82 mounted on stationary base 12. Each sterilant delivery apparatus 80 is configured to deliver sterilizing fluid to the injection units 20 as will be described herein.

The bird restraint apparatus 14 depicted in connection with FIG. 1 may, in one or more embodiments, be similar to those depicted and described in U.S. Pat. No. 5,651,731 (Gorans et al.), U.S. Pat. No. 7,232,50 (Gorans et al.), U.S. Pat. No. 7,363,881 (Gorans et al.), etc., with each of the depicted illustrative embodiment of bird restraint apparatus including a beak/head cavity and a pair of arms 15 that rotate into and out of position to retain the head of a bird in the bird restraint apparatus 14 or to release the head of the bird from the bird restraint apparatus 14.

The bird restraint apparatus used in one or more embodiments of the injection systems described herein may, however, take many different forms. Functionally, the bird restraint apparatus need only restrain a bird in position relative to the injection needles of the injection unit of an injection system in a manner that allows for the injection needles to pierce the skin of the bird and deliver subcutaneous injections as described herein. Potentially suitable alternative bird restraint apparatus may include those described in, e.g., US Patent Application Publication No. US 2012/0012070 (Gorans et al.) although many other alternative bird restraint apparatus may also be used in place of the bird restraint apparatus depicted in, e.g., FIG. 1.

Further, although the processing system 10 depicted in FIG. 1 involves rotary movement of the birds in the bird restraint apparatus 14 relative to the injection units 20, other systems that include the injection systems described herein may not involve rotary movement of the injection units and/or bird restraint apparatus. For example, the injection systems described herein may be used in any suitable processing system and/or method such as those described in, e.g., U.S. Pat. No. 7,367,284 (Gorans), titled AUTOMATED POULTRY PROCESSING METHOD AND SYSTEM. The injection systems and methods described herein may also be used in other systems or environments where transport and/or processing of birds is performed and the birds are restrained in a bird restraint suitable to allow for injections to occur.

Figure 2:
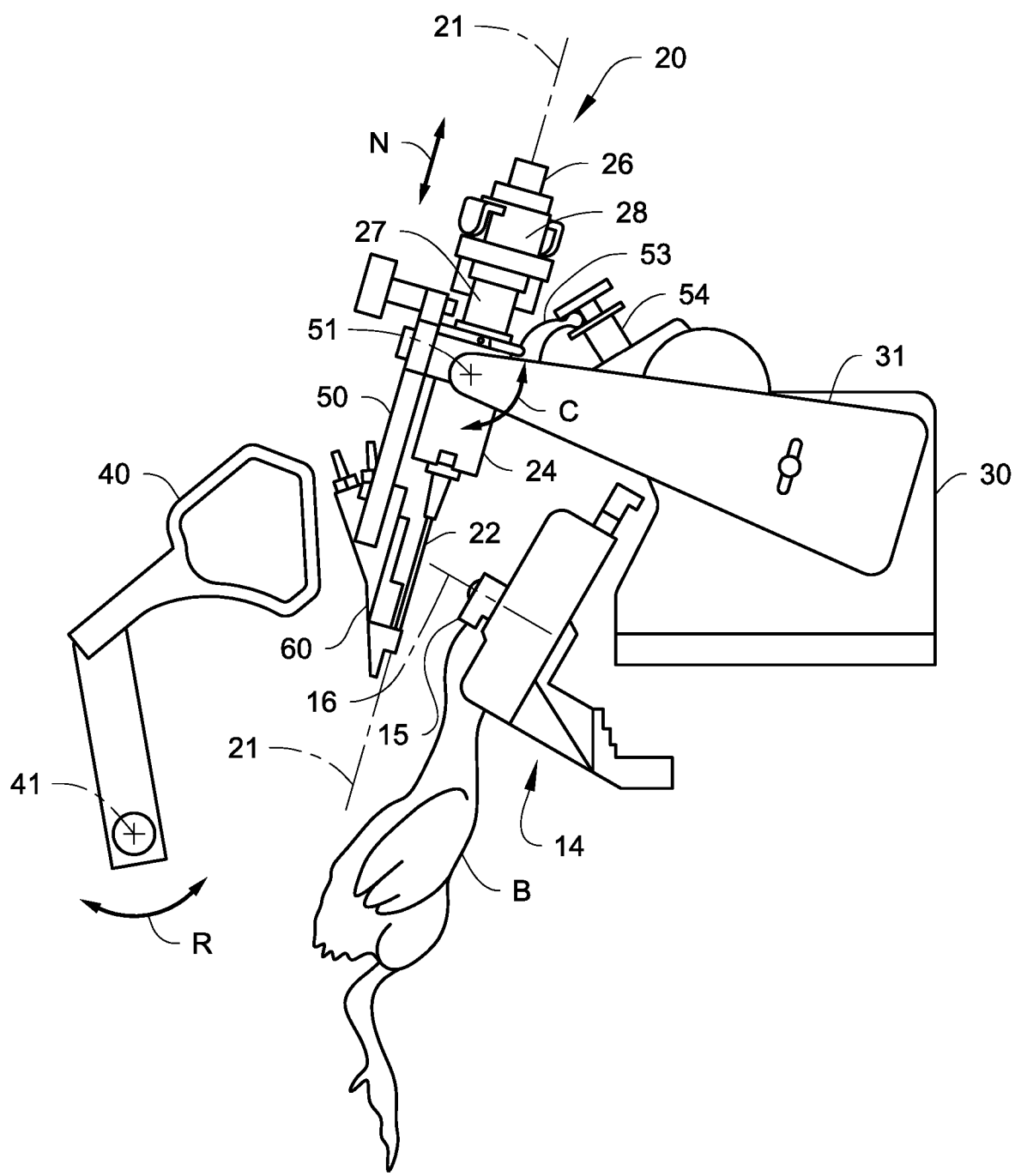
FIG. 2 is a side view of one of the multipoint injection systems in isolation from the larger poultry processing system depicted in FIG. 1 with a bird located in the bird restraint apparatus that forms a part of the injection system.
Figure 3:
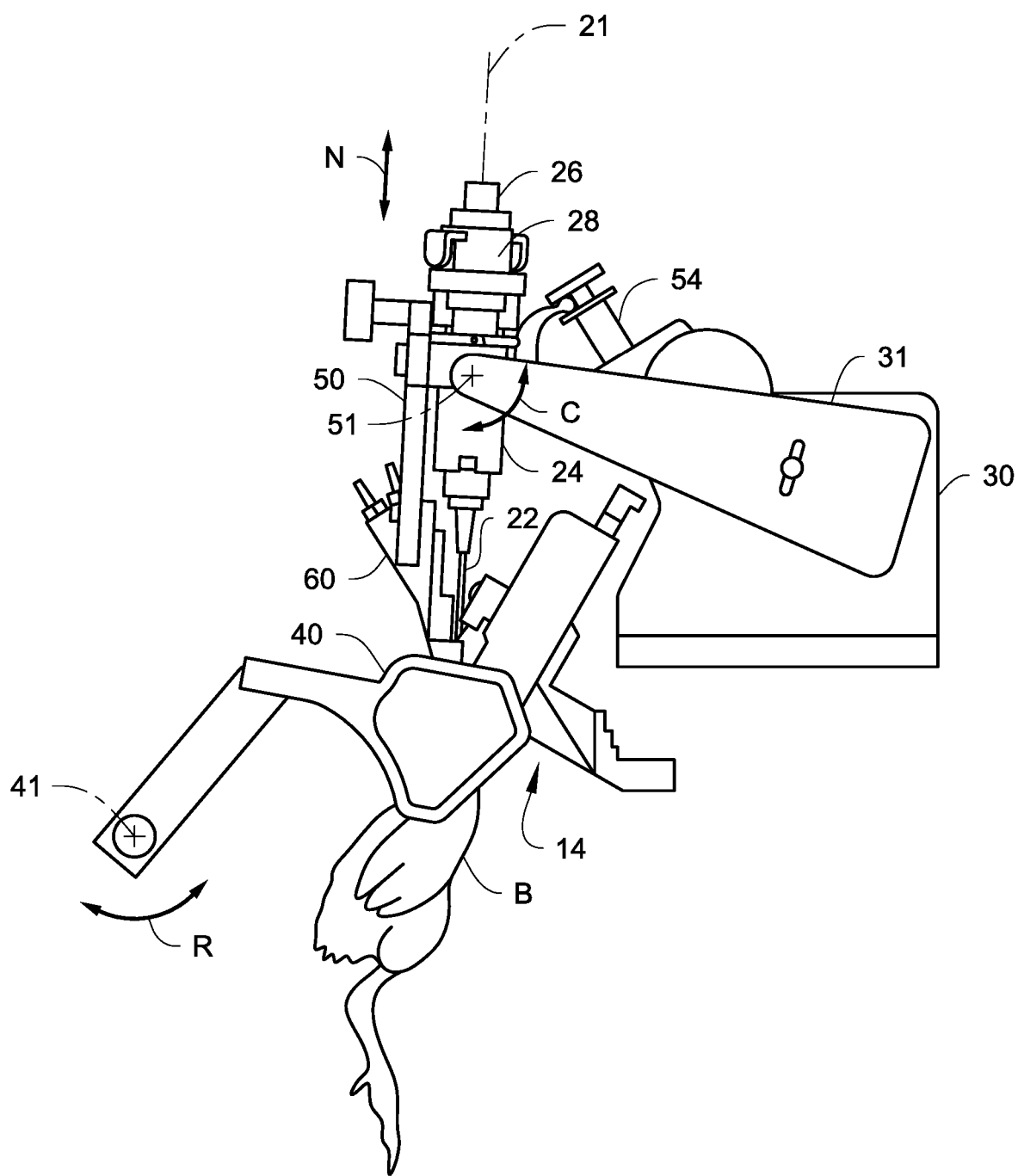
FIG. 3 is a side view of the multipoint injection system of FIG. 2 after rotation of the needle carriage to its actuation position and rotation of the bird stabilizer into its forward position.
Figure 4:
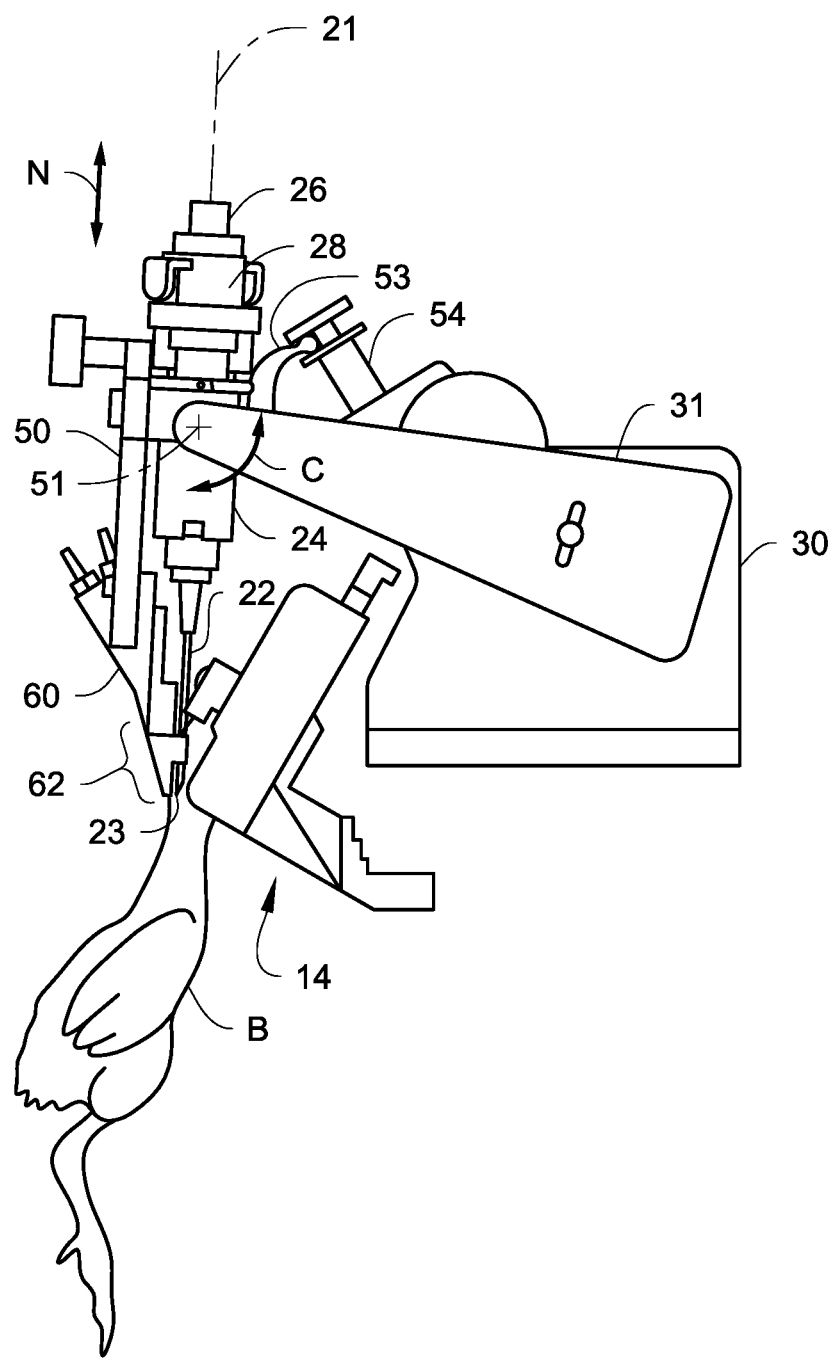
FIG. 4 is a view of the multipoint injection system of FIG. 3 with the bird stabilizer removed to expose the needle carriage.

FIGS. 2-4 are side views of one of the injection systems in isolation from the larger poultry processing system depicted in FIG. 1 with a bird located in the bird restraint apparatus 14 that forms a part of the injection system. In addition to the bird restraint apparatus 14, the injection system depicted in FIGS. 2 and 3 also includes an optional stabilizer 40 that is configured to rotate about stabilizer axis 41 in the direction of bidirectional arrow R to assist in stabilizing a bird B during the injection process. Although not depicted, the stabilizer 40 may be retained in a fixed position relative to the base 30 while the bird restraint apparatus 14 are moved into and out of position relative to the injection units 20 using any suitable support structure. In other words, the position of stabilizer axis 41 may, in one or more embodiments, be fixed relative to the base 30 on which injection unit 20 is mounted. The stabilizer 40 is depicted in its forward position stabilizing the bird B in FIG. 3. FIG. 4 is a side view of the injection system of FIGS. 2-3 with the stabilizer 40 removed to allow visualization of the needle guide 60 and injection needle 22 during the injection process.

As discussed in connection with FIG. 1, the depicted illustrative embodiment of injection unit 20 is supported by a base 30 and arms 31 relative to the bird restraint apparatus 14 which, in the depicted illustrative embodiment, includes arms 15 configured to capture and retain the head and beak of a bird in the bird restraint apparatus 14 and position the bird B relative to the injection unit 20 to facilitate the injection process. In particular, in the depicted illustrative embodiment the arms 15 are configured to rotate about axes 16 into and out of position to retain a bird in the bird restraint apparatus 14 as may be described in, e.g., U.S. Pat. No. 5,651,731 (Gorans et al.), U.S. Pat. No. 7,232,50 (Gorans et al.), and/or U.S. Pat. No. 7,363,881 (Gorans et al.). For clarity, neither the base 12 on which the base 30 is mounted nor the turntable on which the bird restraint apparatus 14 is mounted are depicted in FIGS. 2-4.

With reference to FIGS. 1-4, the injection unit 20 includes a pair of needle assemblies, with each needle assembly including an injection needle 22 and a needle actuator (including, in the depicted illustrative embodiment, actuator body 24, actuator sleep 27, and head 28) that is configured to move the injection needle 22 between an injection position and a retracted position along an injection axis 21 in the direction of bidirectional arrow N.

Each of the depicted needle actuators includes an actuator sleeve 27 and head 28 configured to retain the barrel connector 26 of injection needle 22 in position relative to the actuator body 24. As seen in FIG. 2, the injection needle 22 is depicted in its retracted position, while FIG. 3 depicts the injection needle 22 and its injection position. In the depicted illustrative embodiment, the upper portion of actuator sleeve 27 is exposed above actuator body 24, while in FIG. 3, the lower portion of actuator sleeve 27 is exposed below actuator body 24 with the head 28 attached to actuator sleeve 27 drawn closer towards the actuator body 24 in FIG. 3.

The illustrative embodiment of the injection system depicted in FIGS. 2-4 also includes a needle guide 60 that includes passages configured to guide the injection needles 22 as the injection needles 20 to move between their injection positions and retracted positions as discussed herein. As seen in FIG. 2, the distal ends of the injection needles 22 are located within the guide passages in needle guide 60, while the distal ends 23 of the injection needles 22 are extended out of the guide passages in the needle guide 60 as seen in FIG. 4. Further details with respect to one or more embodiments of the needle guides that may be used in connection with the multipoint injection systems described herein will be discussed elsewhere herein.

In the depicted illustrative embodiment, the needle actuators 24 of the depicted needle assemblies and the needle guide 60 are mounted on a needle carriage 50 that is attached to the arms 31 and base 30 in a manner that allows for rotation of the needle carriage 50 and the needle assemblies and needle guide 60 attached thereto about carriage axis 51 in the directions defined by bidirectional arrow C. In particular, the needle carriage 50 is, in the depicted illustrative embodiment, operably connected to a carriage actuator 54 that is configured to rotate the needle carriage 50 about the carriage axis 51 between a standby position as seen in FIG. 2 and an actuation position as seen in FIGS. 3-4. In the depicted illustrative embodiment, carriage actuator 54 is mounted on base 30 and acts on carriage arm 53 which is, in turn, operably connected to needle carriage 50, although many other alternative arrangements could be provided.

Figure 5:
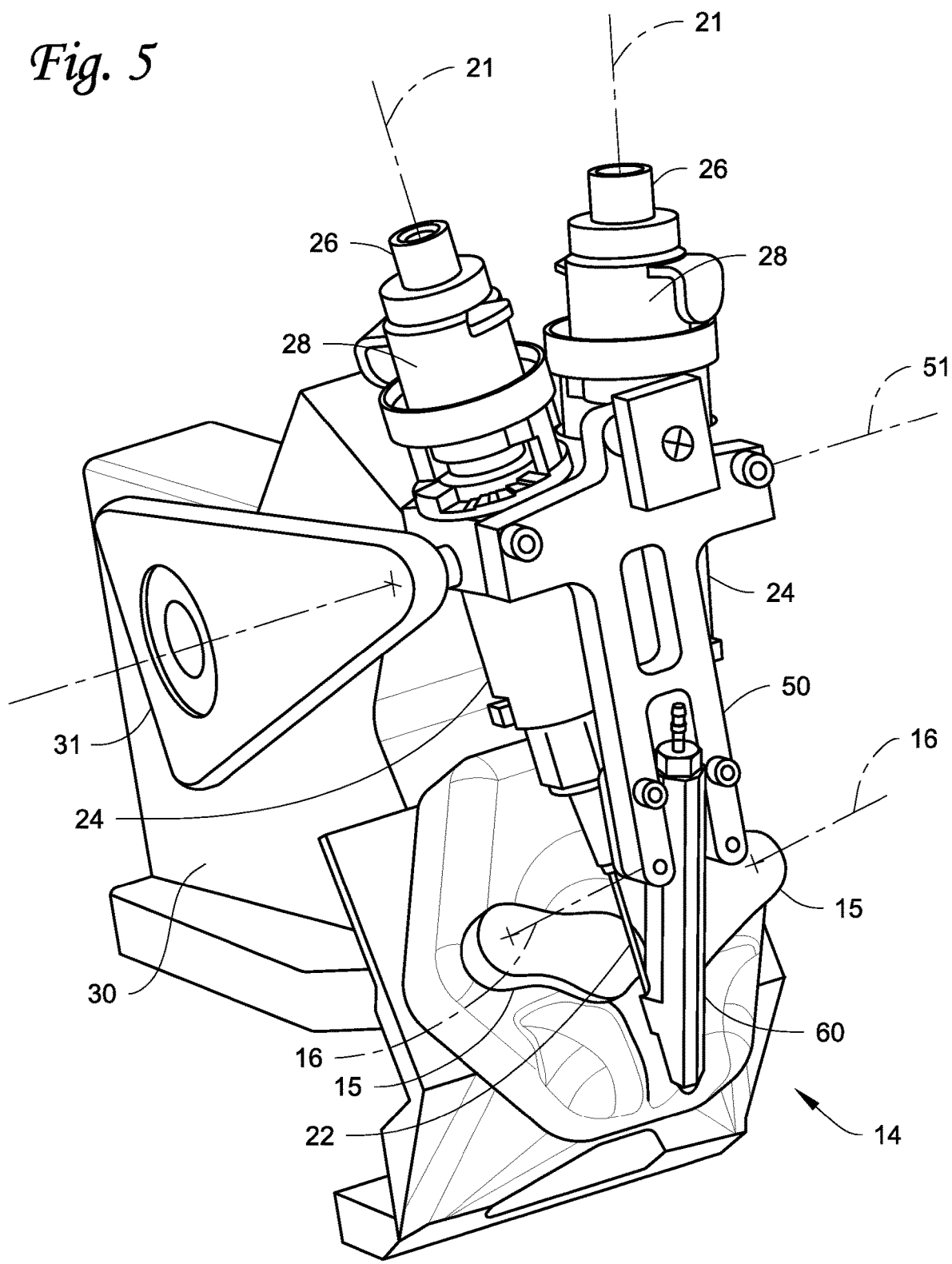
FIG. 5 is a perspective view of the injection system of FIGS. 2-4 with the bird removed.

FIG. 5 is an enlarged perspective view of the injection system of FIGS. 2-4 with the bird removed from the bird restraint apparatus 14. As seen in this perspective view, the injection system includes a pair of needle assemblies, each of which includes an injection needle 22 and a needle actuator along with associated components as discussed in connection with FIGS. 2-4. Both of the needle assemblies are mounted on a needle carriage 50 that rotates about carriage axis 51 as discussed in connection with those figures. Further, each of the injection needles is configured for movement along an injection axis 21. In one or more embodiments, the depicted injection system may be described as a multipoint injection system because it includes two needle assemblies. In one or more alternative embodiments, however, the injection systems described herein may include only one needle assembly, while in still other embodiments, injection systems described herein may include three or more needle assemblies.

Figure 6:
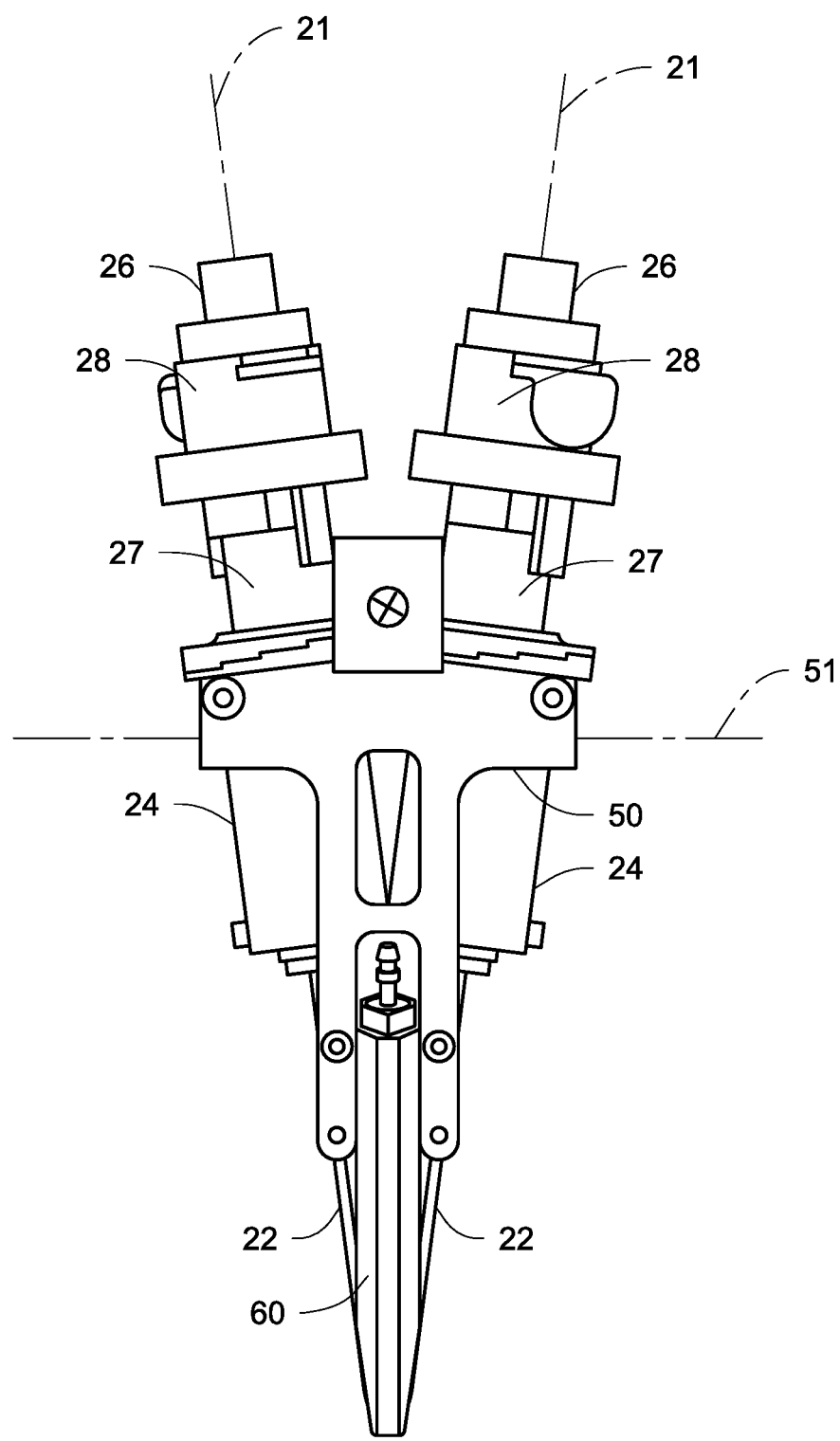
FIG. 6 is a front elevation view of the injection system of FIGS. 2-5 with the bird stabilizer apparatus removed.
Figure 7:
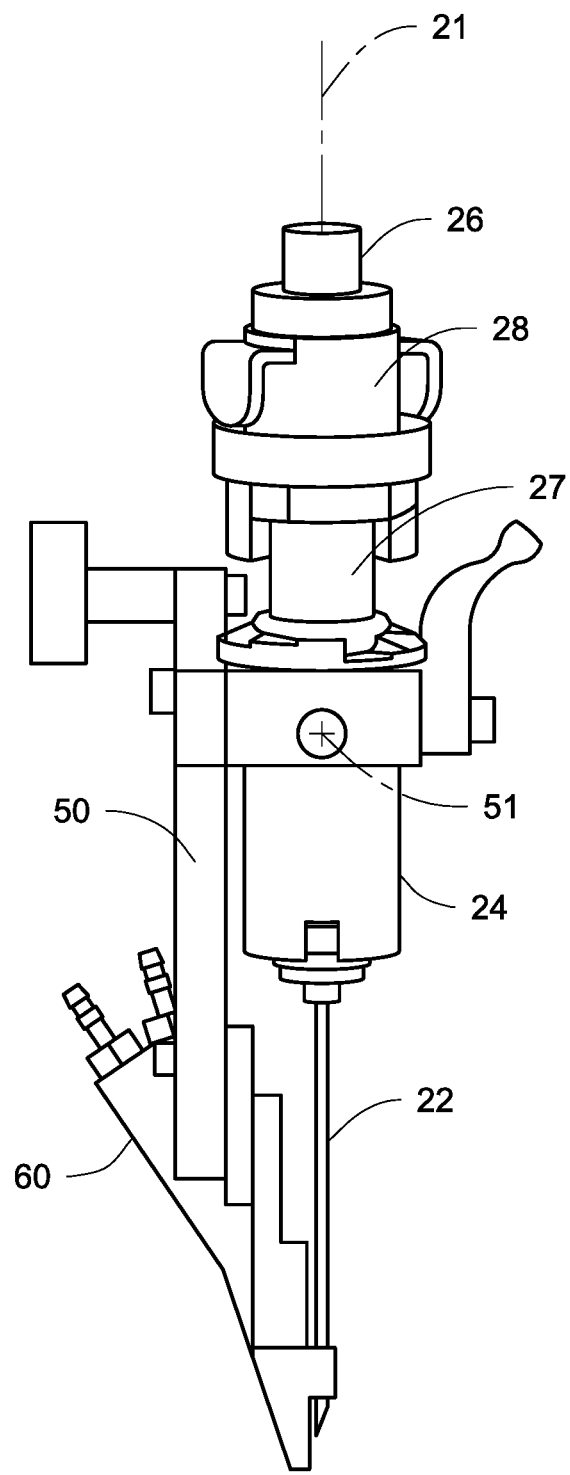
FIG. 7 is a side elevation view of the injection system of FIG. 6.

The injection system depicted in FIG. 5 is depicted in FIGS. 6-7 with the base 30, arms 31 and bird restraint 14 removed for clarity. FIGS. 6-7 are provided to depict one illustrative arrangement between the carriage axes and injection axes in one or more embodiments of injection systems as described herein. In particular, the injection axes 21 are, as best seen in FIG. 7, positioned such that they extend through (e.g., intersect with) carriage axis 51. It should be understood that slight variations in positioning of the injection axes and the carriage axis such that the axes do not actually intersect may, in one or more embodiments of the injection systems described herein, be tolerated and still provide the advantages described herein. In one or more embodiments, the injection axes 21 may be described as "extending through" the carriage axis 51 if the axes pass within 3 mm or less, 2 mm or less, or 1 mm or less of each other.

Such arrangements of the injection axes and the carriage axis may, in one or more embodiments, reduce unwanted movement of an injection needle off of its injection axis 21 during the injection process. As described above, movement of an injection needle off of its injection axis may result in bleeding and/or unwanted tissue damage at an injection site. Although depicted in connection with multiple injection axes, it should be understood that the same advantages would be provided in systems that include only one needle assembly having an injection axis that extends through a carriage axis in one or more embodiments of injection systems as described herein.

Figure 8:
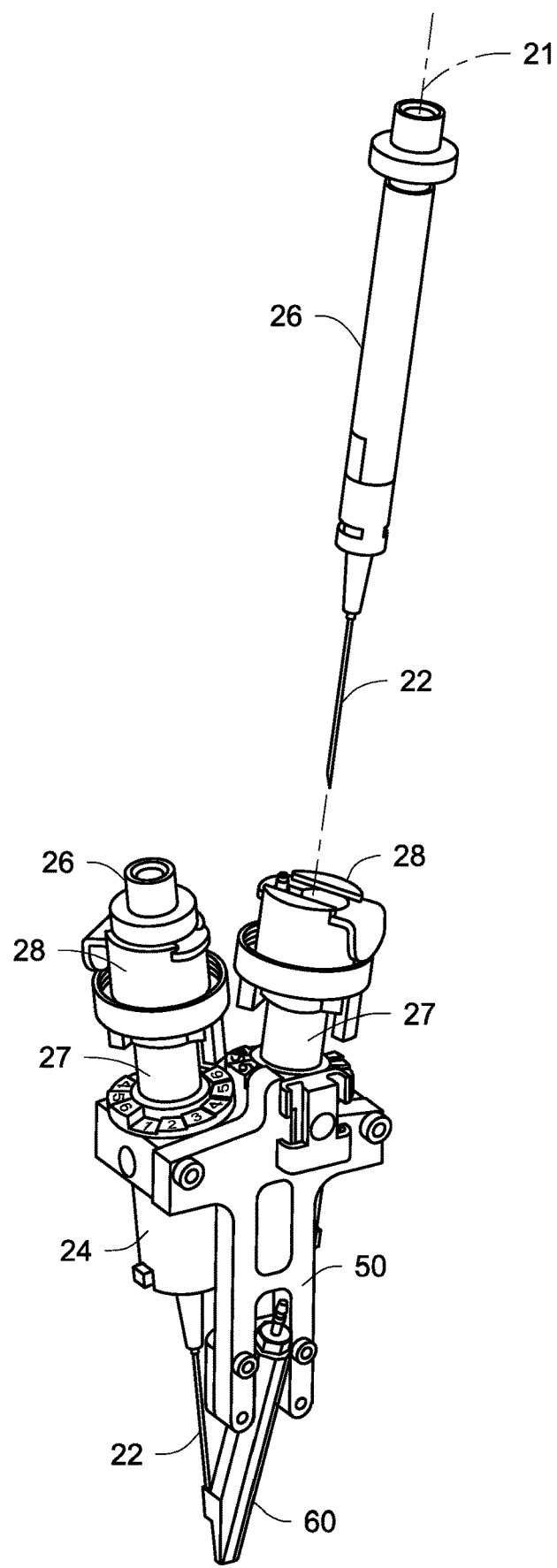
FIG. 8 depicts the injection system of FIGS. 6-7 with an injection needle and barrel connector removed from one of the needle assemblies.

FIG. 8 depicts the injection system of FIGS. 6-7 with an injection needle 22 and its associated barrel connector 26 removed from the needle actuator of one of the needle assemblies. In one or more embodiments of needle assemblies used in injection systems as described herein, the needle actuator (including, in the depicted illustrative embodiment, actuator 24, sleeve 27, and head 28) May be configured to hold and injection needle 22 and its barrel connector 26 along the injection axis 21. Doing so may, in one or more embodiments, simplify installation and routing of vaccine lines and, in one or more embodiments, may reduce unwanted movement of the injection needle off of its injection axis which, as discussed herein, may reduce the likelihood of bleeding and/or tissue damage at an injection site. In one or more embodiments, the barrel connector 26 may include Luer lock features that mate with Luer lock features on the needle actuator to retain the barrel connector 26 and its associated injection needle 22 in the needle actuator.

Figure 9:
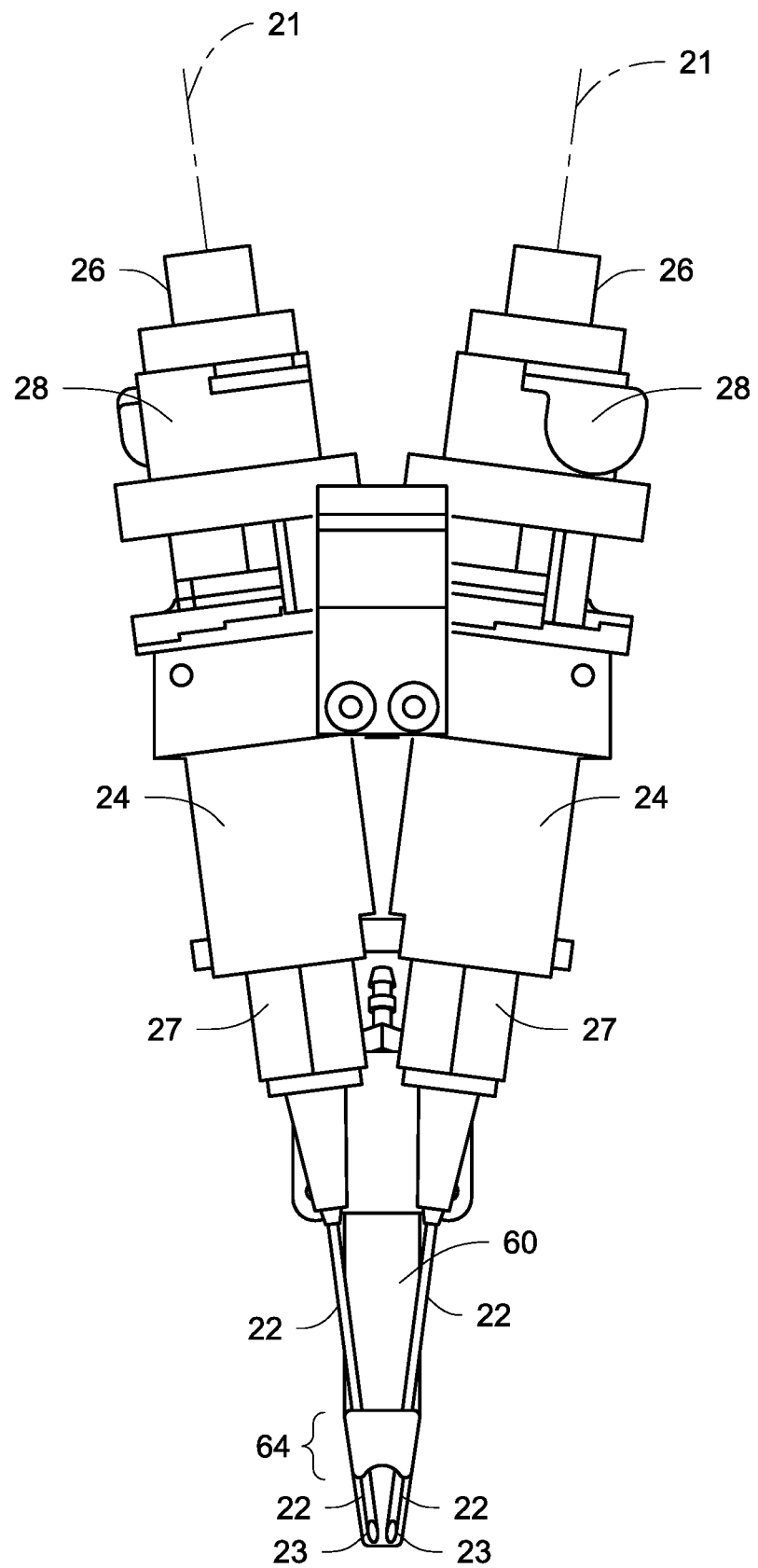
FIG. 9 is a rear view of the injection system of FIGS. 6-7 with the injection needles in their injection positions.

FIG. 9 is a rear view of the injection system of FIGS. 6-8 with the injection needles 22 in their injection positions such that the distal ends 23 of the injection needles 22 are exposed proximate the end of needle guide 60. Furthermore, heads 28 of the needle actuators are located closer to the actuator bodies 24 and the lower ends of the actuator sleeves 27 extend from the actuator bodies 24.

Figure 10:
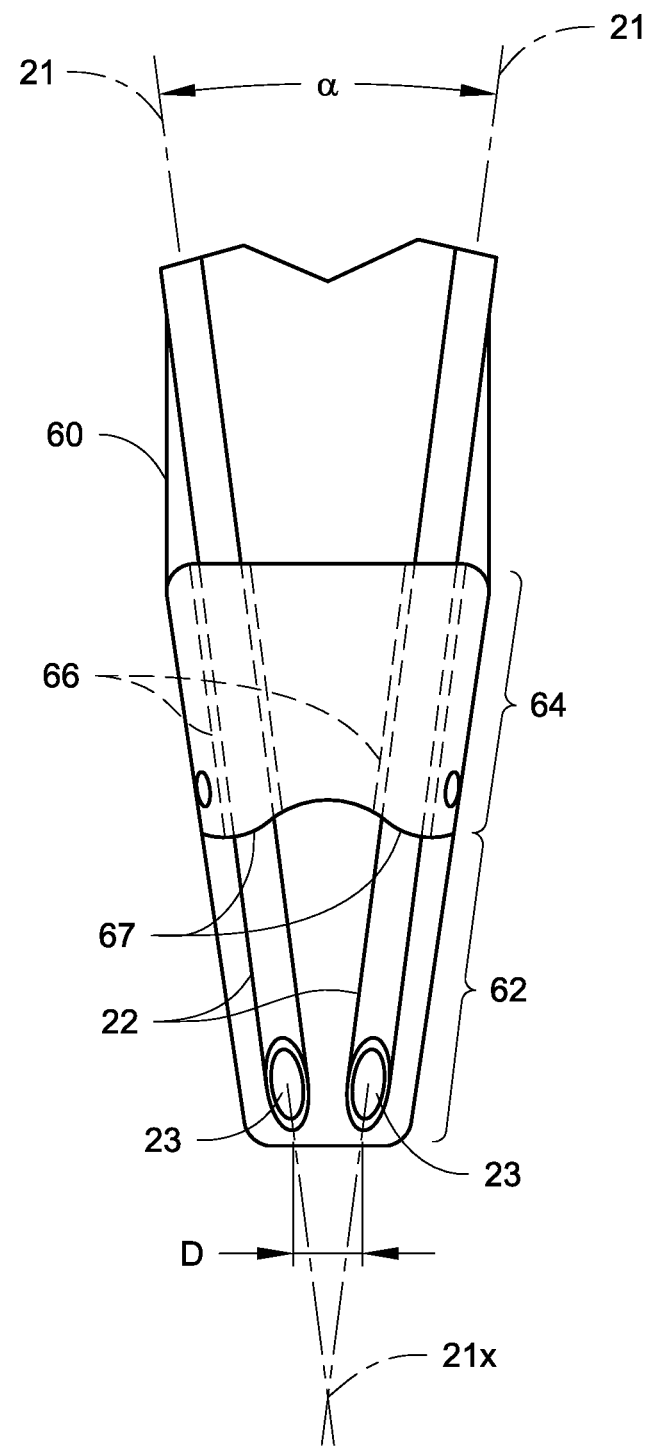
FIG. 10 is an enlarged view of the portion of the injection system depicted in FIG. 9 that includes the injection needles and needle guide passages.
Figure 11:
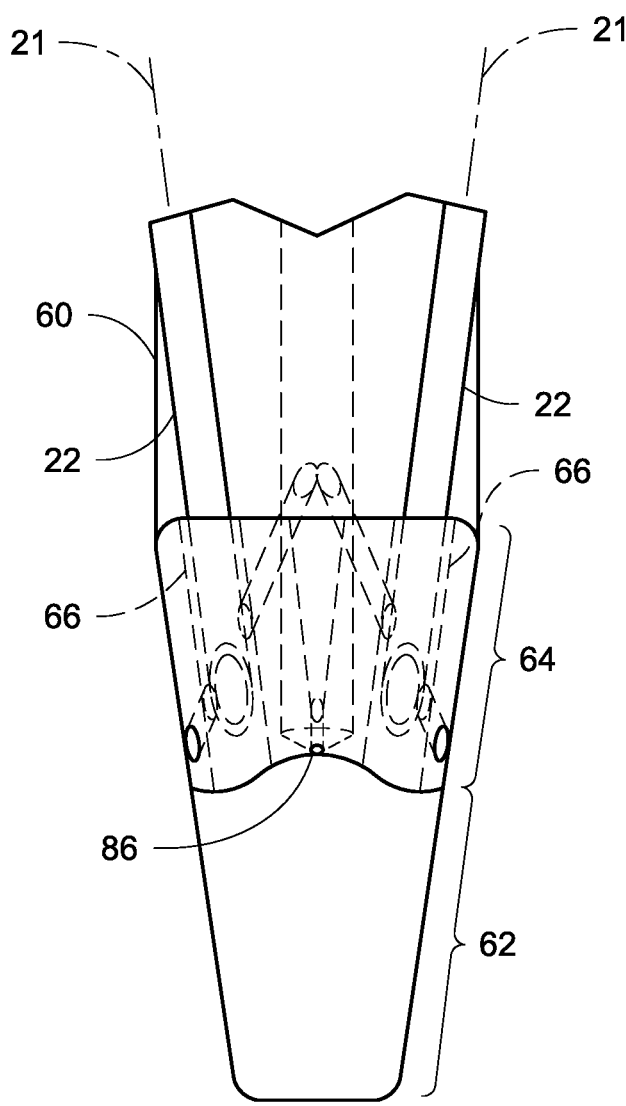
FIG. 11 is a view of the portion of the injection system depicted in FIG. 10 that includes the injection needles and needle guide passages with the injection needles in their retracted positions.

FIG. 10 is an enlarged view of the lower portions of the injection needles 22 of the injection system depicted in FIG. 9 in which the distal ends 23 of the injection needles 22 are, in the depicted illustrative embodiment, extended out of the guide passages 66 located in guide section 64 of needle guide 60. In one or more embodiments of injection systems as described herein that include needle guides, the needle guide 60 may include a guide section 64 having guide passages 66 through which the injection needles 20 move when moving between their retracted and injection positions as described herein. FIG. 11 is, for example, an enlarged view of the portion of the injection system depicted in FIG. 10 in which the injection needles 22 are in their retracted positions in which the distal ends 23 of the injection needles 22 are withdrawn into the needle guide passages 66 located in guide section 64 of the needle guide 60.

In addition, the needle guide 60 may also include a support section 62 configured to limit deflection of the injection needles 22 away from the skin of a bird during the injection process. Referring to, e.g., FIG. 4, the support section 62 may contact the skin of a bird when the needle carriage 50 is moved to its actuation position to limit movement of the injection needles 22 away from the bird as the injection needles 22 are moved from their retracted positions to their injected positions. Contact between the bird and the support section 62 may, however, not be required in all circumstances.

Other features and/or arrangements which may be found in one or more embodiments of the injection systems described herein which are also depicted in FIG. 10 include the distance between the distal ends 23 of a pair of injection needles 22, as well as arrangements between the injection axes 21 along which injection needles 22 move.

In one or more embodiments of injection systems that include multiple injection needles, the spacing between the distal ends of the injection needles when the injection needles are in their injection positions may be controlled to facilitate delivery of injectate to multiple distinct locations in a bird or other animal. For example, in one or more illustrative embodiments, the distance between the lowest portion of the openings found at the distal ends 23 of the injection needles 22 may be spaced apart from each other by a distance D of 1 mm or more, 2 mm or more, or 3 mm or more. At an upper end, the distance D between the lowest portion of the openings found at the distal ends 23 of the injection needles 22 may be 6 mm or less, 4 mm or less, or 2 mm or less.

Figure 12:
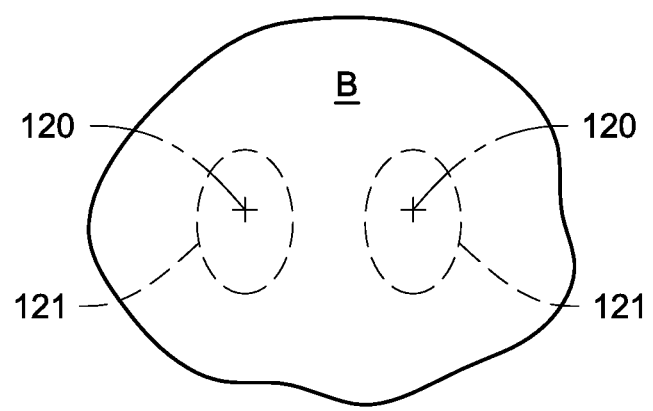
FIG. 12 is a schematic diagram depicting the skin of a bird or other animal after delivery of injectate using two needles such as those depicted in FIGS. 9-11.

Spacing between the distal ends 23 of the injection needles 22 may facilitate the formation of separate and distinct pockets of injected material when the injection systems as described herein are used to deliver injectate to a bird or other animal. With reference to FIG. 12, the surface of a bird B is depicted along with to injection sites 120 that are spaced apart from each other due to the spacing between the distal ends 23 of injection needles 22. The injected material may form separate and distinct pockets 121 proximate each of the injection sites 120 such that the injected material may, in one or more embodiments, not mix immediately upon injection into the bird B. As discussed herein, delivery of two or more different types of injected material into separate and distinct pockets may be useful where the injected material may, for example, be more effective if not mixed immediately upon injection. Even in those instances where the same material is injected into both sites 120, it may be beneficial to deliver to smaller amounts of the same injectate at two different locations on a bird B.

Another feature that may be found in one or more embodiments of the injection systems as described herein is also depicted in connection with FIG. 10. In particular, the injection axes 21 may be oriented such that they are not parallel with each other and, more particularly, may be oriented such that the injection axes 21 converge when moving towards the distal ends 23 of the injection needles 22. In one or more embodiments, the injection axes 21 may converge at an included angle α (alpha) that is greater than 0° and less than 180°. In one or more embodiments, the included angle α (alpha) may be 30° or less, 25° or less, 20° or less, 15° or less. At a lower end, the included angle α (alpha) may be 5° or more, 10° or more, or 15° or more.

Another feature of one or more embodiments of the injection systems as described herein is also depicted in connection with FIG. 10. In particular, the injection axes 21 may, in one or more embodiments be oriented such that the injection axes 21 intersect at a location 21x as depicted in FIG. 10. It should be understood that in other alternative embodiments, the injection axes may not intersect with each other.

Still another feature of one or more embodiments of the injection systems as described herein is also depicted in may be described in connection with FIG. 10. In particular, the guide section 64 of the needle guide 60 includes a guide passage 66 through which each of the injection needles 22 moves when moving between their respective retracted and injection positions. In one or more embodiments, the guide passages 66 guide the injection needles 22 such that deflection of the distal ends 23 of the injection needles 22 from the injection axes 21 is limited during the injection process. In one or more embodiments, the guide passages 66 may be described as having a distal open 67 and, further, the distal and 23 of an injection needle 22 may be described as passing through the distal opening 67 of the guide passage 66 when the injection needle is moving between its injection position and a retracted position. Further, the distal ends 23 of injection needles 22 of one or more embodiments of injection systems as described herein may be located within a guide passage 66 when the injection needles are in their retracted positions.

To limit deflection sufficiently, one or more embodiments of needle guides 60 used in injection systems as described herein may include guide passages 66 having distal openings 67 that are located within 30 mm or less of the distal ends 23 of injection needles 22 when the injection needles 22 are in their injection positions. In one or more alternative embodiments, the distal opening 67 may be located within 20 mm or less of the distal ends, 15 mm or less of the distal ends, or even 10 mm or less of the distal ends.

Further, one or more embodiments of needle guide 60 may preferably include separate and distinct guide passages 66 for each of the injection needles 22 in an injection system as described herein. In other words, only one injection needle 22 passes through each of the guide passages 66 in one or more embodiments of the injection systems described herein.

Yet another feature of one or more embodiments of the injection systems as described herein may also be described in connection with FIG. 10. In particular, the injection needles 22 may have distal ends 23 that end in a beveled tip to facilitate the piercing of skin and other tissue during the injection process. The beveled tips at the distal ends 23 of the injection needles 22 may, in one or more embodiments, the oriented such that the openings formed at the distal ends face away from the needle guide 60 as depicted in, e.g., FIG. 10. This orientation may further facilitate piercing of skin and other tissue during the injection process when using the injection systems as described herein.

Figure 13:
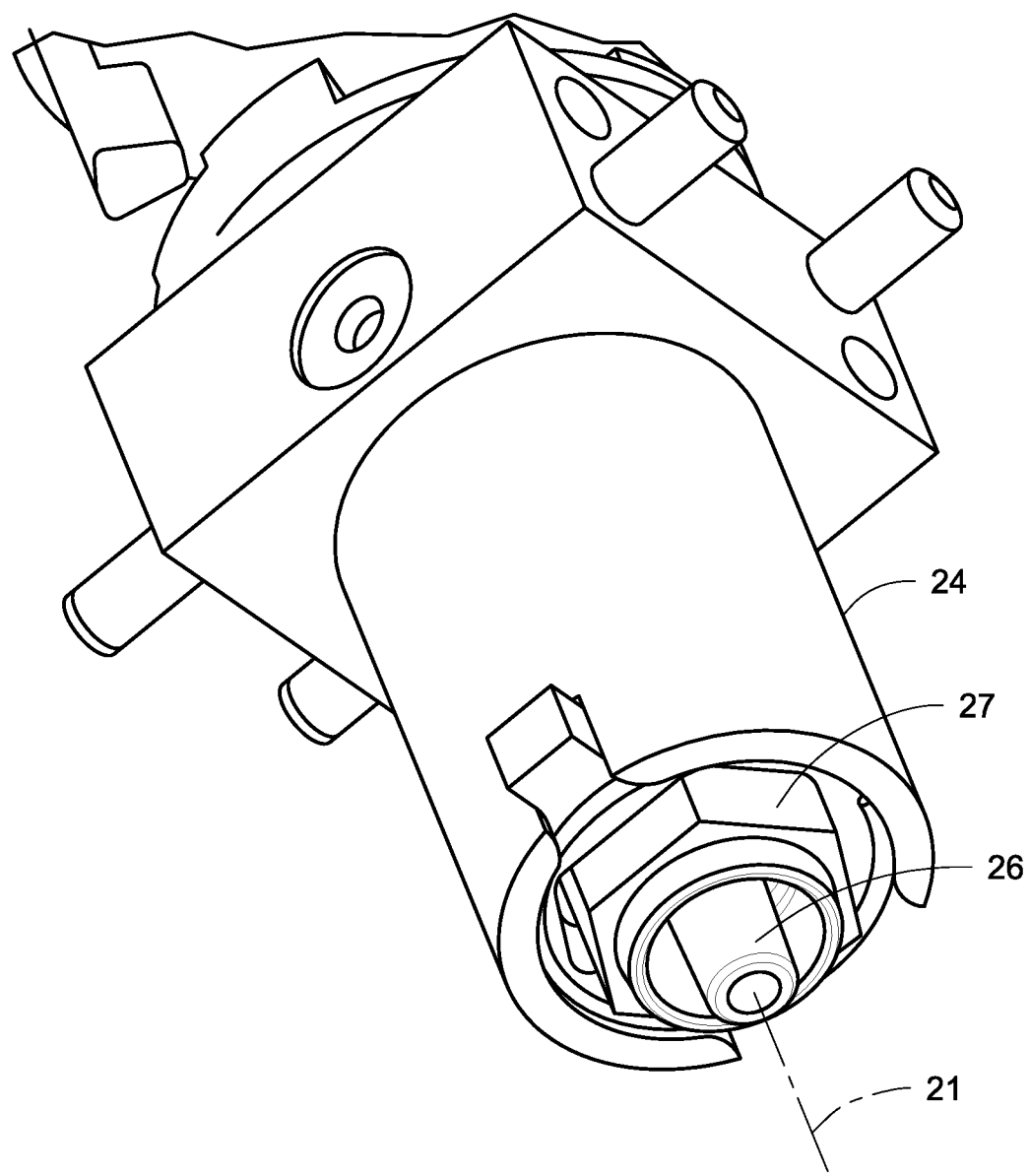
FIG. 13 is a partial perspective view of a portion of one needle actuator depicting one illustrative embodiment of an alignment mechanism that may be used to maintain rotational position of an injection needle in one or more embodiments of an injection system as described herein.

One or more embodiments of the injection systems described herein may include features configured to retain the orientation of the beveled tips at the distal ends 23 of the injection needles 22 in a desired orientation. One illustrative embodiment of features configured to retain the orientation of the beveled tips in a desired orientation is depicted in FIG. 13 which is a partial perspective view of a portion of the bottom of actuator body 24 with the actuator sleeve 27 located therein, along with the bottom end of barrel connector 26 (with the injection needle removed from the barrel connector 26 in this view). Movement of the actuator sleeve 27 along injection axis 21 moves the injection needle between its retracted and injection positions as discussed herein.

To maintain a selected orientation of the beveled tip at the distal end of an injection needle, the sleeve 27 may include alignment features configured to maintain that selected orientation. In particular, the depicted illustrative embodiment includes a sleeve 27 having a hexagonal shape and located within a hexagonal orifice in the actuator body 24 such that rotation of the sleeve 27 about the injection axis 21 is limited. Further, in the depicted illustrative embodiment the barrel connector 26 is also fixed in its orientation such that rotation of the connector barrel (and any injection needle attached thereto) about the injection axis 21 is also limited. This combination of features provides only one illustrative embodiment of an alignment mechanism that may be used to maintain rotational position of an injection needle in one or more embodiments of an injection system and many others could be envisioned and used in place of the depicted set of alignment mechanism features.

Figure 14:
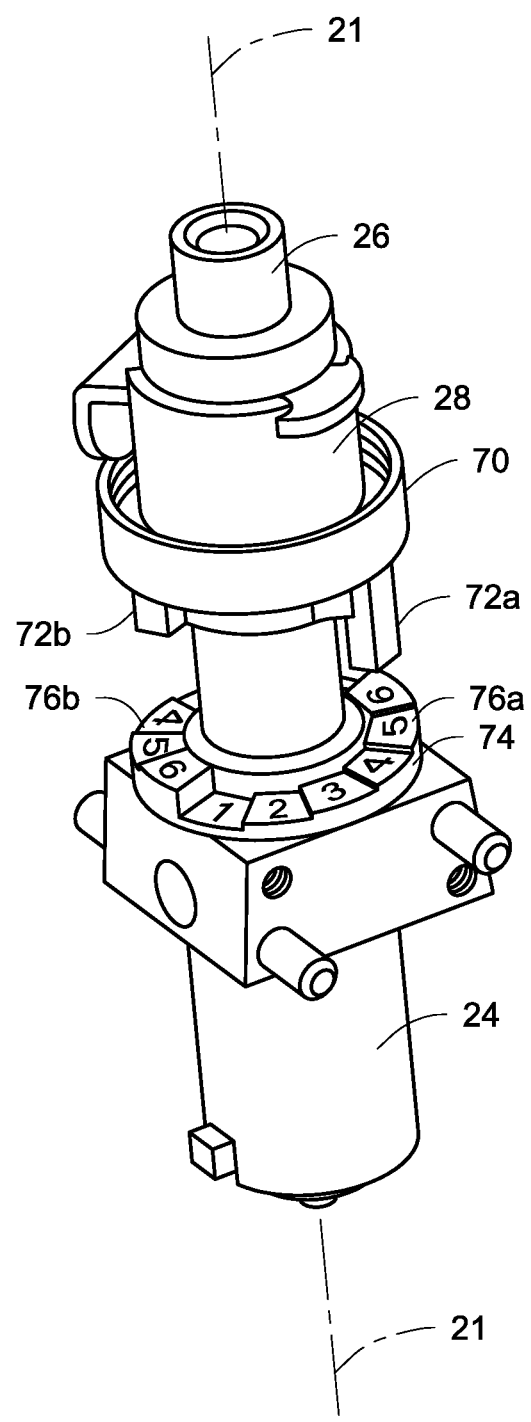
FIG. 14 is a perspective view of one illustrative embodiment of a depth adjustment yoke and support configured to change a location of a distal end of an injection needle along its injection axis of one illustrative embodiment of an injection system as described herein.

One or more embodiments of the injection systems described herein may include structures configured to allow for adjustment of the location of the distal ends 23 of the injection needles 20 in their injection positions to control the depth to which the injection needles are inserted during the injection process. FIG. 14 depicts one illustrative embodiment of structures designed to provide that adjustment in the form of a depth adjustment yoke 70 and support 74 configured to change a location of a distal end 23 of an injection needle 22 along its injection axis 21. In the depicted illustrative embodiment, the adjustment yoke 70 is attached to the head 28 of the needle actuator, while the support 74 is attached to the actuator body 24 with the actuator sleeve 27 extending between the actuator body 24 and the head 28.

In the depicted illustrative embodiment, the depth adjustment yoke 70 is configured to rotate relative to the head 28 about the injection axis 21 without changing its position along the injection axis 21 relative to the head 28, while the support 74 is fixed in position relative to the actuator body 24 and the injection axis 21. It will, however, be understood that both the depth adjustment yoke 70 and the support ring 74 may rotate relative to the injection axis 21, although such a system may prove more difficult to adjust when both components may rotate about the injection axis 21. As a result, it may be preferred that only one of the components 70 or 74 rotate about the injection axis 21.

Rotation of the adjustment yoke 70 about the injection axis 21 provides for adjustment of the location of the distal and 23 of an injection needle attached to connector barrel 26 because rotation of the adjustment yoke 70 changes the minimum distance between the head 28 and the actuator body 24 of the needle actuator. That minimum distance between the head 28 and the actuator body 24 is limited in the depicted illustrative embodiment by legs 72a and 72b which act on steps 76a and 76b on support 74. As seen in FIG. 14, those steps 76a and 76b are located at different heights relative to the actuator body 24 which puts the steps 76a and 76b at different axial locations along the injection axis 21 the legs 72a and 72b rest on a pair of steps 76a and 76b located on opposite sides of the injection axis 21 and at the same relative height to provide for adjustment of the minimum distance between the head 28 and the actuator body 24 when the injection needle is in its injection position.

With respect to the particular depicted embodiment, when legs 72a and 72b are positioned to act on steps "1" on support 74, the head 28 will be located at its closest position relative to the actuator body 24, resulting in a maximum depth setting for an injection needle attached to the barrel connector 26. At the opposite end, when legs 72a and 72b are positioned to act on steps "6" on support 74, the head 28 will be located at its furthest position relative to the actuator body 24, resulting in a minimum depth setting for an injection needle attached to the barrel connector 26.

In the depicted illustrative embodiment, supporting the head 28 of the needle actuator on opposite sides of the injection axis 21 may also be beneficial because doing so may reduce deflection of the distal end of an injection needle attached to the barrel connector as the actuator head 28 moves towards the actuator body 24 during movement of an injection needle from its retracted position to its injection position. That reduction in needle deflection may occur because the forces acting on the head 28 (and, therefore, barrel connector 26 carrying injection needle) are balanced about the injection axis 21 as the legs 72 of the adjustment yoke 70 contact the steps 76 on support 74.

One or more embodiments of the injection systems described herein may include components configured to sterilize the injection needles after they have been used to inject material into a bird or other animal. As used herein, the term "sterilize" (and variations thereof) is not used in the absolute sense in that the sterilizing components and any sterilant they deliver need not necessarily sterilize the injection needles, but the sterilizing components and any sterilant they deliver may reduce the likelihood of cross-contamination between birds or other animals injected using the injection needles described herein.

Figure 15:
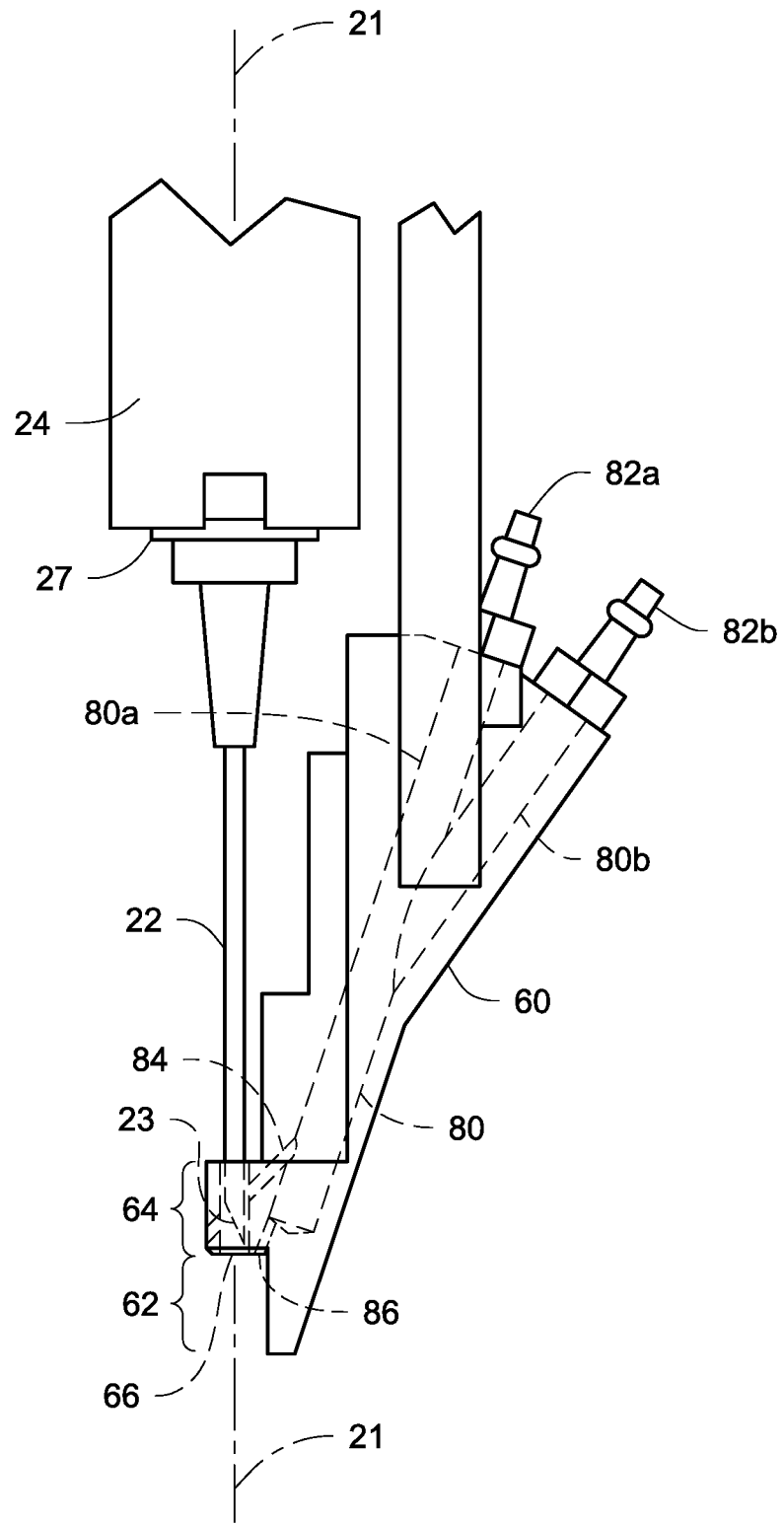
FIG. 15 is an enlarged side view of one illustrative embodiment of a sterilant passage in the depicted illustrative embodiment of a needle guide mounted on a needle carriage of one illustrative embodiment of an injection system as described herein.

In the depicted illustrative embodiment as seen in, e.g., FIG. 15, the needle guide 60 may include various passages and fittings for receiving sterilizing fluid and delivering the sterilizing fluid to the injection needles in a manner that may reduce cross-contamination. In particular, the needle guide 60 includes, in the depicted illustrative embodiment, passage 80a as well as passage 80b, both of which meet to form common passage 80 which leads to outlet port 84. Fluid passing through the common sterilant passage 80 and out of outlet port 84 is directed into the guide passage 66 of needle guide 60 such that the fluid is directed at a distal end 23 of the injection needle 22 located in the guide passage 66.

In the view depicted in FIG. 15, only one injection needle 22 and its corresponding guide passage 66 are depicted. It should, however, be understood that where needle guide 60 includes a second guide passage 66 and a second injection needle 22, a second outlet port 84 is provided from common passage 80 to allow for the delivery of fluid from common passage 80 into that second guide passage 66 and on to the second injection needle 22 located therein.

In the depicted illustrative embodiment, to inlet ports 82a and 82b are provided, with inlet port 82a feeding passage 80a and inlet port 82b feeding passage 80b. Both passages 80a and 80b and their respective inlet ports 82a and 82b are provided to allow for the delivery of a sterilizing fluid through one of the inlet ports and a purging fluid (such as, e.g., compressed air or one or more gasses, liquids, etc.) through the other inlet port.

For example, in one or more embodiments, a sterilizing fluid may be delivered through inlet port 82a, where it passes into passage 80a and then into common passage 80 for delivery to outlet 84. In one or more embodiments, the sterilizing fluid delivered into the passage 80a may be atomized before being delivered into the passage 80a. After delivery of the sterilizing fluid onto the injection needle 22 through outlet port 84, it may be beneficial to purge at least the outlet port 84 of any remaining sterilizing fluid and, in one or more embodiments, possibly remove at least a portion of any residual sterilizing fluid remaining on the injection needle 22 using a purging fluid. The second inlet port 82b can be used for that purging fluid which, when delivered, would pass through passage 80b and into common passage 80 for delivery to the outlet port 84.

In one or more alternative embodiments, sterilizing fluid in liquid form may be delivered into one of the passages 80a or 80b while an atomizing fluid (such as, e.g., compressed air or one or more gasses, liquids, etc.) is delivered into the other passage 80a or 80b to atomize the sterilizing fluid delivered to the needle(s) 22 in guide port(s) 66.

In still one or more alternative embodiments, the needle guide 60 may include only one passage 80 fed by only one inlet port 82, with an atomized and/or liquid form of sterilizing fluid being delivered into the passage 80 for delivery to one or more needles in one or more guide passages of the needle guide.

In addition to outlet ports 84 configured to deliver sterilizing fluid onto the injection needles as described herein, a separate outlet 86 may also be provided in fluid communication with the common passage 82 deliver sterilizing fluid onto the support section 62 of the needle guide 60 such that debris on the support section 62 may be removed by the delivery of the sterilizing fluid and/or the purging fluid as described herein.

Many other fluidic structures could be used to deliver both a sterilizing fluid and a purging fluid to one or more injection needles of one or more embodiments of an injection system as described herein and the illustrative embodiments depicted and described herein represent only one potential set of fluidic structures to deliver sterilizing fluid and a purging fluid as needed.

Figure 16:
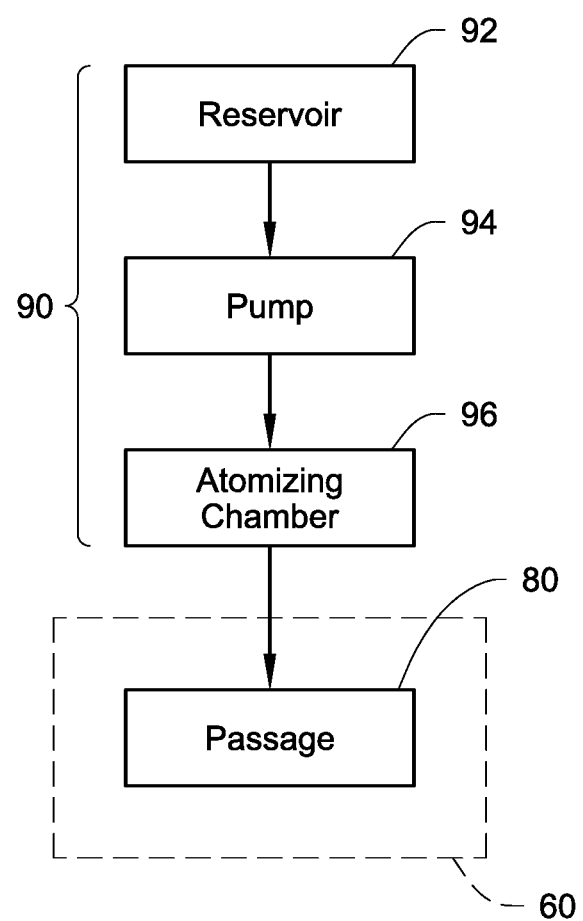
FIG. 16 is a schematic diagram of one illustrative embodiment of a sterilant delivery apparatus that may be used to deliver atomized sterilizing fluid to the injection needles of one or more embodiments of injection systems as described herein.
Figure 17:
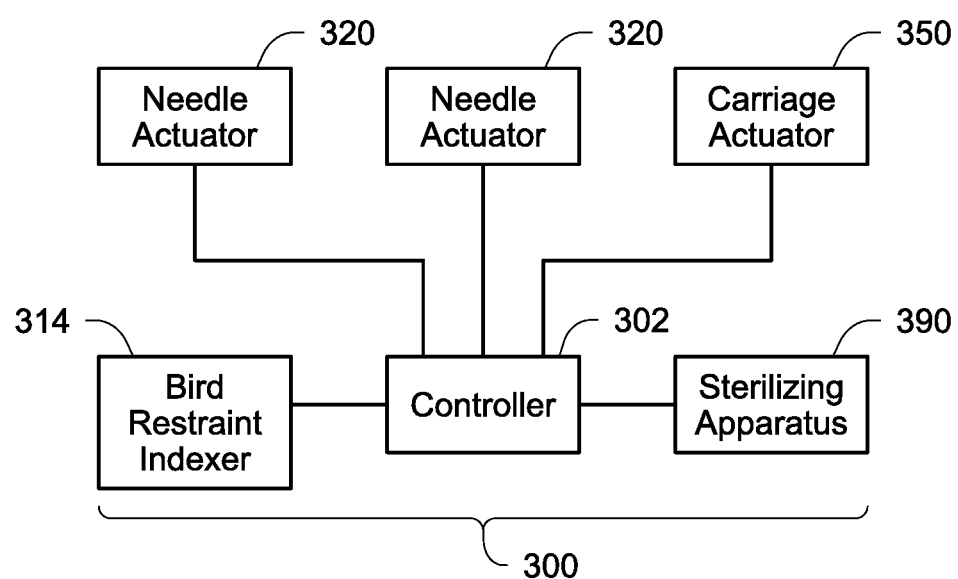
FIG. 17 is a schematic diagram of a controller that may be used to control various components of one or more embodiments of an injection system as described herein.

FIG. 16 depicts one illustrative embodiment of a sterilant delivery apparatus that may be used to deliver atomized sterilizing fluid to the injection needles of one or more embodiments of injection systems as described herein. The sterilant delivery apparatus 90 depicted in FIG. 16 may, in one or more embodiments, include a reservoir 92, pump 94, and atomizing chamber 96. The pump 94 is configured to deliver sterilizing fluid from the reservoir 92 to the atomizing chamber 96 where the sterilizing fluid is atomized. A fluid path is then also provided and configured to deliver the atomized sterilizing fluid from the atomizing chamber 96 to the passage 80 in the needle guide 60 of the embodiments of injection systems as described herein. In one or more embodiments, the sterilizing fluid may be, e.g., isopropyl alcohol, although other sterilizing fluids may alternatively be used.

Atomizing the sterilizing fluid before delivering it to the passage 80 may, in one or more embodiments, provide advantages to one or more embodiments of injection systems as described herein. For example, in one or more embodiments, locating the atomizing chamber 96 along with the pump 94 in a sterilant delivery apparatus 90 and delivering atomized sterilizing fluid to the passage 80 eliminates the need for check valves or other fluid control devices in the needle guides where they may become fouled or otherwise negatively affect operation of the sterilant delivery process.

In one or more alternative embodiments of injection systems as described herein, sterilization may be performed without the use of a sterilizing fluid. For example, one or more embodiments of injection systems as described herein may employ one or more UV light sources configured to deliver ultraviolet light as needed to sterilize injection needles and other components between birds.

FIG. 17 is a schematic block diagram of various components that may be used in one or more embodiments of the injection systems as described herein. The depicted illustrative embodiment of system 300 includes a controller 302 that may be operably connected to various components in the injection systems. The controllers used in the injection systems described herein may be provided in any suitable form and may, for example, include memory and a control unit. In one or more embodiments, the control unit of a controller may, for example, be in the form of one or more microprocessors, Field-Programmable Gate Arrays (FPGA), Digital Signal Processors (DSP), microcontrollers, Application Specific Integrated Circuit (ASIC) state machines, etc.

Among the other components depicted in FIG. 10 are two needle actuators 320 along with a carriage actuator 350. Rotation of the first and/or second capture members 22 and 24 may be accomplished using any suitable actuator mechanisms. Examples of some potentially suitable actuators that may be used for the needle actuators and/or carriage actuators of one or more embodiments of injection systems as described herein may include, e.g., hydraulic pistons, solenoids, etc. Any structure capable of providing the motion required to move the injection needles, needle carriage, bird restraint, etc. as described herein could be used as an actuator. Some potentially suitable examples may include, e.g., reversible motors, reciprocating mechanisms, etc.

The controller 302 operably connected to the needle actuators 320 may be configured to actuate one or both of the needle actuator 320 from their retracted positions to their injection positions either at the same time and/or at different times. In some instances, one of the needle actuators may be actuated by the controller while the other needle actuator may be left idle where, for example, only one injectate is to be delivered using only one injection needle.

The controller 302 is also operably connected to the carriage actuator, with the controller being configured to actuate the carriage actuator 350 to move the needle carriage between its standby position and actuation position as described herein.

The sterilant delivery apparatus 390 is also operably connected to the controller 302, with the controller being configured to operate the sterilant delivery apparatus to deliver sterilizing fluid and, optionally, purging fluid, to the injection system as described herein.

The bird restraint indexer 314 that may also be operably connected to the controller 302 may be used to move bird restraints into and out of position relative to the injection units as described herein such that a bird restrained in a bird restraint can be moved into position where an injection unit can be used to deliver injectate to the bird, with the bird being then moved out of position after receiving an injection and a different bird being moved into position relative to the injection unit.

Additional Embodiments

Embodiment 1. An injection system comprising:
- an injection unit comprising:
  - a first needle assembly comprising a first injection needle and a first needle actuator operably connected to the first injection needle, wherein the first needle actuator is configured to move the first injection needle between an injection position and a retracted position along a first injection axis;
  - optionally, a second needle assembly comprising a second injection needle and a second needle actuator operably connected to the second injection needle, wherein the second needle actuator is configured to move the second injection needle between an injection position and a retracted position along a second injection axis;
  - wherein, for injection systems including first and second needle assemblies, a distal end of the first injection needle is spaced apart from a distal end of the second injection needle when the first and second injection needles are in their injection positions by a distance of 1 mm or more, optionally 2 mm or more, or optionally 3 mm or more and, at an optional upper end, 6 mm or less, optionally 4 mm or less, or optionally 2 mm or less; and
- a bird restraint apparatus operably connected to the injection unit, wherein the bird restraint apparatus is configured to restrain a bird in a selected position relative to the injection unit.

Embodiment 2. An injection system comprising:
- an injection unit comprising:
  - a first needle assembly comprising a first injection needle and a first needle actuator operably connected to the first injection needle, wherein the first needle actuator is configured to move the first injection needle between an injection position and a retracted position along a first injection axis;
  - optionally, a second needle assembly comprising a second injection needle and a second needle actuator operably connected to the second injection needle, wherein the second needle actuator is configured to move the second injection needle between an injection position and a retracted position along a second injection axis, wherein, for injection systems including first and second needle assemblies, the first injection axis and the second injection axis are not parallel to each other; and
- a bird restraint apparatus operably connected to the injection unit, wherein the bird restraint apparatus is configured to restrain a bird in a selected position relative to the injection unit.

Embodiment 3. A system according to embodiment 2, wherein a distal end of the first injection needle is spaced apart from a distal end of the second injection needle when the first and second injection needles are in their injection positions by a distance of 1 mm or more, optionally 2 mm or more, or optionally 3 mm or more and, at an optional upper end, 6 mm or less, optionally 4 mm or less, or optionally 2 mm or less.

Embodiment 4. A system according to any one of embodiments 1 to 3, wherein the first injection axis and the second injection axis intersect.

Embodiment 5. A system according to any one of embodiments 1 to 4, wherein the first injection axis and the second injection axis form an included angle greater than zero degrees and less than 180 degrees.

Embodiment 6. A system according to any one of embodiments 1 to 4, wherein the first injection axis and the second injection axis form an included angle of 30 degrees or less, optionally 25° or less, optionally 20° or less, or optionally 15° or less, and, at an optional lower end, the included angle may be 5° or more, optionally 10° or more, or optionally 15° or more.

Embodiment 7. A system according to any one of embodiments 1 to 6, wherein the first needle assembly and, optionally, the second needle assembly are mounted on a needle carriage, wherein the needle carriage is operably connected to a carriage actuator, wherein the carriage actuator is configured to rotate the needle carriage about a carriage axis between a standby position and an actuation position, wherein the first and second injection needles are configured to contact a bird restrained in the bird restraint when the needle carriage moves into the actuation position, and wherein the first and second injection needles are positioned subcutaneously in a bird restrained in the bird restraint apparatus when the needle carriage is in its actuation position and the first and second injection needles in their injection positions.

Embodiment 8. A system according to embodiment 7, wherein the carriage axis extends through the first injection axis and the second injection axis.

Embodiment 9. A system according to any one of embodiments 1 to 8, wherein the injection unit comprises a needle guide, wherein the needle guide comprises:
- a first guide passage configured to guide the first injection needle when the first injection needle moves between the injection position and the retracted position; and
- optionally, a second guide passage configured to guide the second injection needle when the second injection needle moves between the injection position and the retracted position.

Embodiment 10. A system according to embodiment 9, wherein the first guide passage comprises a distal opening, and wherein a distal end of the first injection needle passes through the distal opening when moving between the injection position and the retracted position;
and wherein, optionally, the second guide passage comprises a distal opening, and wherein a distal end of the second injection needle passes through the distal opening of the second guide passage when moving between the injection position and the retracted position.

Embodiment 11. A system according to either one of embodiments 9 to 10, wherein the first guide passage and the second guide passage are separate and distinct passages in the needle guide.

Embodiment 12. A system according to any one of embodiments 9 to 11, wherein the first needle assembly, the optional second needle assembly, and the needle guide are mounted on a needle carriage, wherein the needle carriage is configured to rotate about a carriage axis between a standby position and an actuation position, wherein the needle guide is configured to contact a bird restrained in the bird restraint when the needle carriage moves into the actuation position, and wherein the first and second injection needles are positioned subcutaneously in a bird restrained in the bird restraint apparatus when the needle carriage is in its actuation position and the first and second injection needles in their injection positions.

Embodiment 13. A system according to embodiment 11, wherein the carriage axis extends through the first injection axis and the second injection axis.

Embodiment 14. A system according to any one of embodiments 1 to 13, wherein the first needle actuator comprises a depth adjustment yoke and support, wherein the depth adjustment and yoke and support are configured to change a location of a distal end of the first injection needle along the first injection axis.

Embodiment 15. A system according to embodiment 14, wherein rotation of one or both of the depth adjustment yoke and the support about the first injection axis changes a location of a distal end of the first injection needle along the first injection axis.

Embodiment 16. A system according to any one of embodiments 14 or 15, wherein the depth adjustment yoke comprises first and second legs acting on the support, wherein the first and second legs are located on opposite sides of the first injection axis.

Embodiment 17. A system according to embodiment 16, wherein the first and second legs comprise a different length when measured along the first injection axis and wherein the support comprises a stepped ring comprising a plurality of steps located at different positions along the first injection axis.

Embodiment 18. A system according to embodiment 17, wherein rotation of one or both of the depth adjustment yoke and the stepped ring about the first injection axis changes a location of a distal end of the first injection needle along the first injection axis.

Embodiment 19. A system according to any one of embodiments 1 to 18, wherein the second needle actuator comprises a depth adjustment yoke and support, wherein the depth adjustment and yoke and support are configured to change a location of a distal end of the second injection needle along the second injection axis.

Embodiment 20. A system according to embodiment 19, wherein rotation of one or both of the depth adjustment yoke and the support about the second injection axis changes a location of a distal end of the second injection needle along the second injection axis.

Embodiment 21. A system according to any one of embodiments 19 or 20, wherein the depth adjustment yoke comprises first and second legs acting on the support, wherein the first and second legs are located on opposite sides of the second injection axis.

Embodiment 22. A system according to embodiment 16, wherein the support comprises a stepped ring comprising a plurality of steps arranged around the second injection axis and located at different positions along a length of the second injection axis, wherein rotation of the stepped ring and/or the depth adjustment yoke changes a distance between the stepped ring and the depth adjustment yoke.

Embodiment 23. A system according to embodiment 22, wherein rotation of one or both of the depth adjustment yoke and the stepped ring about the second injection axis changes a location of a distal end of the second injection needle along the second injection axis.

Embodiment 24. A system according to any one of embodiments 9 to 23, wherein the needle guide comprises a sterilant passage extending between an inlet port and an outlet port, wherein fluid passing through the sterilant passage from the inlet port to the outlet port is directed at a distal end of the first injection needle.

Embodiment 25. A system according to embodiment 24, wherein the sterilant passage comprises a first sterilant passage, the inlet port comprises a first inlet port, and the outlet port comprises a first outlet port;

and wherein the needle guide comprises a second sterilant passage extending between a second inlet port and a second outlet port, wherein fluid passing through the second sterilant passage from the second inlet port to the second outlet port is directed at a distal end of the second injection needle.

Embodiment 26. A system according to any one of embodiments 1 to 25, wherein the system further comprises a sterilant delivery apparatus comprising:

a pump configured to deliver sterilizing fluid from a reservoir to an atomizing chamber, wherein the atomizing chamber is configured to atomize the sterilizing fluid; and a fluid path configured to deliver the atomized sterilizing fluid from the atomizing chamber onto a distal end of the first injection needle through a sterilant port.

Embodiment 27. A system according to embodiment 26, wherein the fluid path comprises a first fluid path and the sterilant port comprises a first sterilant port, and wherein the sterilant delivery system comprises a second fluid path configured to deliver atomized sterilizing fluid from the atomizing chamber onto a distal end of the second injection needle through a second sterilant port.

Embodiment 28. A system according to embodiment 27, wherein the first fluid path comprises a sterilant passage in the needle guide, wherein the sterilant passage extends between an inlet port and a first outlet port, wherein fluid passing through the sterilant passage to the first outlet port is directed at a distal end of the first injection needle;

and wherein the second fluid path comprises a sterilant passage in the needle guide, wherein the sterilant passage extends between the inlet port and a second outlet port, wherein fluid passing through the sterilant passage to the second outlet port is directed at a distal end of the second injection needle.

Embodiment 29. A system according to any one of embodiments 1 to 28, wherein the system further comprises a controller operably connected to the first needle actuator and the second needle actuator, wherein the controller is configured to:

actuate the first needle actuator to move the first injection needle from its retracted position to its injection position; and actuate the second needle actuator to move the second injection needle from its retracted position to its injection position.

Embodiment 30. A system according to embodiment 29, wherein the controller is configured to actuate the first and second needle actuators at the same time.

Embodiment 31. A system according to embodiment 29, wherein the controller is configured to actuate the first and second needle actuators at different times.

Embodiment 32. A system according to any one of embodiments 29 to 31, wherein the system comprises the needle carriage and the carriage actuator recited in any one of embodiments 7 to 8, wherein the controller is operably connected to the carriage actuator, and wherein the controller is configured to actuate the carriage actuator to move the needle carriage between the standby position and the actuation position.

Embodiment 33. A system according to any one of embodiments 29 to 32, wherein the system comprises the sterilant delivery apparatus recited in any one of embodiments 25 to 28, wherein the pump is operably connected to the controller, and wherein the controller is configured to operate the pump to deliver sterilizing fluid to the atomizing chamber.

Embodiment 34. A method comprising:
restraining a bird in the bird restraint apparatus of an injection system according to any one of embodiments 1 to 33;
moving the bird restraint apparatus to an injection location proximate the injection unit;
advancing the first injection needle to its injection position after moving the bird restraint apparatus to the injection location;
optionally, advancing the second injection needle to its injection position after moving the bird restraint apparatus to the injection location;
delivering a first selected material to a first location in the bird through the first injection needle after advancing the first injection needle into the injection position; and
optionally, delivering a second selected material to a second location in the bird through the second injection needle after advancing the second injection needle into the injection position.

Embodiment 35. A method according to embodiment 34, wherein the first location and the second location are different.

Embodiment 36. A method according to either one of embodiments 34 and 35, wherein the first selected material and the second selected material are the same.

Embodiment 37. A method according to either one of embodiments 34 and 35, wherein the first selected material and the second selected material are different.

Embodiment 38. A method according to any one of embodiments 34 to 37, wherein the method further comprises:
moving the first injection needle from its injection position towards its retracted position after delivering the first selected material;
delivering sterilant onto a distal end of the first injection needle after moving the first injection needle from its injection position towards its retracted position;
optionally, moving the second injection needle from its injection position towards its retracted position after delivering the second selected material; and
optionally, delivering sterilant onto a distal end of the second injection needle after moving the second injection needle from its injection position towards its retracted position.

Embodiment 39. A method according to embodiment 38, wherein the first injection needle is moved from its injection position towards its retracted position and the second injection needle is moved from its injection position towards its retracted position at the same time.

Embodiment 40. A method according to either one of embodiments 38 to 39, wherein the sterilant is atomized before delivery onto the first injection needle and the second injection needle.

Embodiment 41. A method according to any one of embodiments 38 to 40, wherein the sterilant is delivered onto the first injection needle after the first injection needle is in its retracted position.

The complete disclosure of the patents, patent documents, and publications identified herein are incorporated by reference in their entirety as if each were individually incorporated. To the extent there is a conflict or discrepancy between this document and the disclosure in any such incorporated document, this document will control.

Illustrative embodiments of the injection systems and methods of using the same are discussed herein with some possible variations described. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof. It should also be understood that this invention also may be suitably practiced in the absence of any element not specifically disclosed as necessary herein.

What is claimed is:

1. An injection system comprising:
an injection unit comprising:
a first needle assembly comprising a first injection needle and a first needle actuator operably connected to the first injection needle, wherein the first needle actuator is configured to move the first injection needle between an injection position and a retracted position along a first injection axis, wherein the first needle actuator comprises a depth adjustment yoke and support, wherein the depth adjustment and yoke and support are configured to change a location of a distal end of the first injection needle along the first injection axis, and wherein rotation of one or both of the depth adjustment yoke and the support about the first injection axis changes a location of a distal end of the first injection needle along the first injection axis; and
a needle carriage operably connected to a carriage actuator, wherein the first needle assembly is mounted on the needle carriage,
wherein the carriage actuator is configured to rotate the needle carriage about a carriage axis between a standby position and an actuation position,
wherein the first injection needle is configured to contact a bird restrained in a bird restraint when the needle carriage moves into the actuation position, and wherein the first injection needle is positioned subcutaneously in the bird restrained in the bird restraint apparatus when the needle carriage is in its actuation position and the first injection needle is in the injection position,
wherein the carriage axis extends through the first injection axis; and
wherein the bird restraint is operably connected to the injection unit and configured to restrain the bird in a selected position relative to the injection unit.

2. A system according to claim 1, wherein the depth adjustment yoke comprises first and second legs acting on the support, wherein the first and second legs are located on opposite sides of the first injection axis.

3. A system according to claim 2, wherein the first and second legs comprise a different length when measured along the first injection axis and wherein the support comprises a stepped ring comprising a plurality of steps located at different positions along the first injection axis.

4. A system according to claim 3, wherein rotation of one or both of the depth adjustment yoke and the stepped ring about the first injection axis changes a location of a distal end of the first injection needle along the first injection axis.

5. A system according to claim 1, wherein the injection unit comprises a needle guide, wherein the needle guide comprises a first guide passage configured to guide the first injection needle when the first injection needle moves between the injection position and the retracted position.

6. A system according to claim 5, wherein the first guide passage comprises a distal opening, and wherein a distal end of the first injection needle passes through the distal opening when moving between the injection position and the retracted position.

7. A system according to claim 5, wherein the needle guide is mounted on the needle carriage.

8. A system according to claim 5, wherein the needle guide comprises a sterilant passage extending between an inlet port and an outlet port, wherein fluid passing through the sterilant passage from the inlet port to the outlet port is directed at a distal end of the first injection needle.

9. A system according to claim 1, wherein the system further comprises a sterilant delivery apparatus comprising:
  a pump configured to deliver sterilizing fluid from a reservoir to an atomizing chamber, wherein the atomizing chamber is configured to atomize the sterilizing fluid; and
  a fluid path configured to deliver the atomized sterilizing fluid from the atomizing chamber onto a distal end of the first injection needle through a sterilant port.

10. A system according to claim 1, wherein the system further comprises a controller operably connected to the first needle actuator, wherein the controller is configured to actuate the first needle actuator to move the first injection needle from its retracted position to its injection position.

11. A system according to claim 10, wherein the controller is operably connected to the carriage actuator, and wherein the controller is configured to actuate the carriage actuator to move the needle carriage between the standby position and the actuation position.

12. A method of positioning a bird in an injection system, the method comprising:
  restraining a bird in the bird restraint apparatus of an injection system according to claim 1;
  rotating one or both of the depth adjustment yoke and the support about the first injection axis to change a location of a distal end of the first injection needle along the first injection axis;
  moving the bird restraint apparatus to an injection location proximate the injection unit;
  rotating the needle carriage about the carriage axis from the standby position to the actuation position,
  wherein the first injection axis of the first needle assembly intersects the bird in the bird restraint apparatus when the needle carriage is in the actuation position;
  and wherein the carriage axis extends through the first injection axis when the needle carriage is in the standby position and the actuation position.

13. A system according to claim 12, wherein the depth adjustment yoke comprises first and second legs acting on the support, wherein the first and second legs are located on opposite sides of the first injection axis.

14. A system according to claim 13, wherein the first and second legs comprise a different length when measured along the first injection axis and wherein the support comprises a stepped ring comprising a plurality of steps located at different positions along the first injection axis.

15. A system according to claim 14, wherein rotation of one or both of the depth adjustment yoke and the stepped ring about the first injection axis changes a location of a distal end of the first injection needle along the first injection axis.

16. An injection system comprising:
  an injection unit comprising:
    a first needle assembly comprising a first injection needle and a first needle actuator operably connected to the first injection needle, wherein the first needle actuator is configured to move the first injection needle between an injection position and a retracted position along a first injection axis;
    a needle carriage operably connected to a carriage actuator, wherein the first needle assembly is mounted on the needle carriage,
      wherein the carriage actuator is configured to rotate the needle carriage about a carriage axis between a standby position and an actuation position,
      wherein the first injection needle is configured to contact a bird restrained in the bird restraint when the needle carriage moves into the actuation position, and wherein the first injection needle is positioned subcutaneously in a bird restrained in the bird restraint apparatus when the needle carriage is in its actuation position and the first injection needle is in the injection position,
      and wherein the carriage axis extends through the first injection axis; and the injection unit further comprising a needle guide that comprises:
        a first guide passage configured to guide the first injection needle when the first injection needle moves between the injection position and the retracted position, and
        a sterilant passage extending between an inlet port and an outlet port, wherein fluid passing through the sterilant passage from the inlet port to the outlet port is directed at a distal end of the first injection needle; and
  a bird restraint apparatus operably connected to the injection unit, wherein the bird restraint apparatus is configured to restrain a bird in a selected position relative to the injection unit.

17. A system according to claim 16, wherein the first needle actuator comprises a depth adjustment yoke and support, wherein the depth adjustment and yoke and support are configured to change a location of a distal end of the first injection needle along the first injection axis, and wherein the depth adjustment yoke comprises first and second legs acting on the support, wherein the first and second legs are located on opposite sides of the first injection axis.

18. A system according to claim 17, wherein rotation of one or both of the depth adjustment yoke and the support about the first injection axis changes a location of a distal end of the first injection needle along the first injection axis.

19. A system according to claim 17, wherein the first and second legs comprise a different length when measured along the first injection axis and wherein the support comprises a stepped ring comprising a plurality of steps located at different positions along the first injection axis.

20. A system according to claim 19, wherein rotation of one or both of the depth adjustment yoke and the stepped ring about the first injection axis changes a location of a distal end of the first injection needle along the first injection axis.

21. A system according to claim 16, wherein the first guide passage comprises a distal opening, and wherein a distal end of the first injection needle passes through the distal opening when moving between the injection position and the retracted position.

22. A system according to claim 16, wherein the needle guide is mounted on the needle carriage.

23. A system according to claim 16, wherein the system further comprises a sterilant delivery apparatus comprising:
a pump configured to deliver sterilizing fluid from a reservoir to an atomizing chamber, wherein the atomizing chamber is configured to atomize the sterilizing fluid; and
a fluid path configured to deliver the atomized sterilizing fluid from the atomizing chamber onto a distal end of the first injection needle through a sterilant port.

24. A system according to claim 16, wherein the system further comprises a controller operably connected to the carriage actuator, and wherein the controller is configured to actuate the carriage actuator to move the needle carriage between the standby position and the actuation position.

25. An injection system comprising:
an injection unit comprising:
a first needle assembly comprising a first injection needle and a first needle actuator operably connected to the first injection needle, wherein the first needle actuator is configured to move the first injection needle between an injection position and a retracted position along a first injection axis;
a needle carriage operably connected to a carriage actuator, wherein the first needle assembly is mounted on the needle carriage,
wherein the carriage actuator is configured to rotate the needle carriage about a carriage axis between a standby position and an actuation position,
wherein the first injection needle is configured to contact a bird restrained in the bird restraint when the needle carriage moves into the actuation position, and wherein the first injection needle is positioned subcutaneously in a bird restrained in the bird restraint apparatus when the needle carriage is in its actuation position and the first injection needle is in the injection position,
and wherein the carriage axis extends through the first injection axis;
a sterilant delivery apparatus comprising:
a pump configured to deliver sterilizing fluid from a reservoir to an atomizing chamber, wherein the atomizing chamber is configured to atomize the sterilizing fluid, and
a fluid path configured to deliver the atomized sterilizing fluid from the atomizing chamber onto a distal end of the first injection needle through a sterilant port; and
a bird restraint apparatus operably connected to the injection unit, wherein the bird restraint apparatus is configured to restrain a bird in a selected position relative to the injection unit.

26. A system according to claim 25, wherein the first needle actuator comprises a depth adjustment yoke and support, wherein the depth adjustment and yoke and support are configured to change a location of a distal end of the first injection needle along the first injection axis, and wherein the depth adjustment yoke comprises first and second legs acting on the support, wherein the first and second legs are located on opposite sides of the first injection axis.

27. A system according to claim 26, wherein rotation of one or both of the depth adjustment yoke and the support about the first injection axis changes a location of a distal end of the first injection needle along the first injection axis.

28. A system according to claim 26, wherein the first and second legs comprise a different length when measured along the first injection axis and wherein the support comprises a stepped ring comprising a plurality of steps located at different positions along the first injection axis.

29. A system according to claim 28, wherein rotation of one or both of the depth adjustment yoke and the stepped ring about the first injection axis changes a location of a distal end of the first injection needle along the first injection axis.

30. A system according to claim 25, wherein the injection unit comprises a needle guide, wherein the needle guide comprises a first guide passage configured to guide the first injection needle when the first injection needle moves between the injection position and the retracted position, wherein the first guide passage comprises a distal opening, and wherein a distal end of the first injection needle passes through the distal opening when moving between the injection position and the retracted position.

31. A system according to claim 25, wherein the injection unit comprises a needle guide, wherein the needle guide comprises a first guide passage configured to guide the first injection needle when the first injection needle moves between the injection position and the retracted position, and wherein the needle guide is mounted on the needle carriage.

32. A system according to claim 25, wherein the system further comprises a controller operably connected to the carriage actuator, and wherein the controller is configured to actuate the carriage actuator to move the needle carriage between the standby position and the actuation position.

* * * * *